(12) United States Patent
Binch et al.

(10) Patent No.: US 7,528,142 B2
(45) Date of Patent: May 5, 2009

(54) AMINOPYRIMIDINES USEFUL AS KINASE INHIBITORS

(75) Inventors: Hayley Binch, San Diego, CA (US); Michael Mortimore, Burford (GB); Damien Fraysse, Abingdon (GB); Chris Davis, Wiltshire (GB); Michael O'Donnell, Oxfordshire (GB); Simon Everitt, Bucks (GB); Daniel Robinson, Oxfordshire (GB); Joanne Pinder, Oxfordshire (GB); Andrew Miller, Oxfordshire (GB)

(73) Assignee: Vertex Pharmaceuticals Incorporated, Cambridge, MA (US)

( * ) Notice: Subject to any disclaimer, the term of this patent is extended or adjusted under 35 U.S.C. 154(b) by 0 days.

(21) Appl. No.: 11/592,119

(22) Filed: Nov. 3, 2006

(65) Prior Publication Data

US 2007/0249031 A1    Oct. 25, 2007

Related U.S. Application Data

(60) Provisional application No. 60/733,557, filed on Nov. 4, 2005, provisional application No. 60/732,951, filed on Nov. 3, 2005.

(51) Int. Cl.
*C07D 403/14* (2006.01)
*A61K 31/4155* (2006.01)

(52) U.S. Cl. ...................... 514/274; 544/317
(58) Field of Classification Search ................. 544/317; 514/274
See application file for complete search history.

(56) References Cited

U.S. PATENT DOCUMENTS

| | | | |
|---|---|---|---|
| 3,133,081 A | 5/1964 | Lafferty et al. |
| 3,755,322 A | 8/1973 | Winter et al. |
| 3,935,183 A | 1/1976 | Baron et al. |
| 3,998,951 A | 12/1976 | Harnish et al. |
| 4,051,252 A | 9/1977 | Mayer et al. |
| 4,493,726 A | 1/1985 | Burdeska et al. |
| 4,540,698 A | 9/1985 | Ishikawa et al. |
| 4,711,951 A | 12/1987 | Axen et al. |
| 5,124,441 A | 6/1992 | Carlsson et al. |
| 5,710,158 A | 1/1998 | Myers et al. |
| 5,916,908 A | 6/1999 | Giese et al. |
| 5,972,946 A | 10/1999 | Murata et al. |
| 6,093,716 A | 7/2000 | Davis et al. |
| 6,184,226 B1 | 2/2001 | Chakravarty et al. |
| 6,200,977 B1 | 3/2001 | Cushing et al. |
| 6,277,989 B1 | 8/2001 | Chakravarty et al. |
| 6,495,582 B1 | 12/2002 | Hale et al. |
| 6,528,509 B1 | 3/2003 | Hale et al. |
| 6,528,513 B2 | 3/2003 | Cushing et al. |
| 6,558,657 B1 | 5/2003 | Mandeville, III et al. |
| 6,562,971 B2 | 5/2003 | Frauenkron et al. |
| 6,569,499 B2 | 5/2003 | Grammatica et al. |
| 6,579,983 B1 | 6/2003 | Batchelor et al. |
| 6,589,958 B1 | 7/2003 | Frietze |
| 6,593,326 B1 | 7/2003 | Bradbury et al. |
| 6,610,677 B2 | 8/2003 | Davies et al. |
| 6,613,776 B2 | 9/2003 | Knegtel et al. |
| 6,638,926 B2 | 10/2003 | Davies et al. |
| 6,641,579 B1 | 11/2003 | Bernardi et al. |
| 6,642,227 B2 | 11/2003 | Cao et al. |
| 6,653,300 B2 | 11/2003 | Bebbington et al. |
| 6,653,301 B2 | 11/2003 | Bebbington et al. |
| 6,656,939 B2 | 12/2003 | Bebbington et al. |
| 6,660,731 B2 | 12/2003 | Bebbington et al. |
| 6,664,247 B2 | 12/2003 | Bebbington et al. |
| 6,689,778 B2 | 2/2004 | Bemis et al. |
| 6,696,452 B2 | 2/2004 | Davies et al. |
| 6,716,851 B2 | 4/2004 | Cai et al. |
| 6,727,251 B2 | 4/2004 | Bebbington et al. |
| 6,743,791 B2 | 6/2004 | Cao et al. |
| 6,825,190 B2 | 11/2004 | Moon et al. |
| 6,838,464 B2 | 1/2005 | Pease et al. |
| 6,841,579 B1 | 1/2005 | Plowman et al. |
| 6,846,928 B2 | 1/2005 | Bebbington et al. |
| 6,884,804 B2 | 4/2005 | Choon-Moon |
| 6,919,338 B2 | 7/2005 | Mortlock et al. |
| 6,949,544 B2 | 9/2005 | Bethiel et al. |
| 6,989,385 B2 | 1/2006 | Bebbington et al. |
| 7,008,948 B2 | 3/2006 | Bebbington et al. |
| 7,084,159 B2 | 8/2006 | Cao et al. |
| 7,087,603 B2 | 8/2006 | Bebbington et al. |

(Continued)

FOREIGN PATENT DOCUMENTS

EP        0019811   A1     12/1980

(Continued)

OTHER PUBLICATIONS

Traxler, Protein Tyrosine Kinase inhibitors in Cancer treatment, Expert Opinion on Therapeutic Patents, 7(6), pp. 571-588, 1997.*
Agarwal, N. et al., "Suitably Functionalized Pyrimidines as Potential Antimycotic Agents", Bioorg. Med. Chem. Lett., 10, 8, 703-706 (2000).
Ali, N.M. et al, "Palladium-Catalyzed Cross Coupling Reactions of Arylboronic Acids with Pi-Deficient Heteroaryl Chlorides" Tetrahedron, 48 (37), 8117-8126 (1992).
Alonso, M. et al., "GSK-3 Inhibitors: Discoveries and Developments", Current Medicinal Chemistry, 11, 755-763 (2004).

(Continued)

*Primary Examiner*—Deepak Rao
(74) *Attorney, Agent, or Firm*—H. Joon Chung

(57) ABSTRACT

The present invention relates to compounds useful as inhibitors of protein kinases. The invention also provides pharmaceutically acceptable compositions comprising those compounds and methods of using the compounds and compositions in the treatment of various disease, conditions, and disorders. The invention also provides processes for preparing compounds of the invention.

11 Claims, No Drawings

U.S. PATENT DOCUMENTS

| | | | |
|---|---|---|---|
| 7,091,343 | B2 | 8/2006 | Bebbington et al. |
| 7,098,330 | B2 | 8/2006 | Bebbington et al. |
| 7,115,739 | B2 | 10/2006 | Bebbington et al. |
| 7,179,826 | B2 | 2/2007 | Bebbington et al. |
| 7,253,187 | B2 | 8/2007 | Cao et al. |
| 7,304,061 | B2 | 12/2007 | Hale et al. |
| 2002/0052386 | A1 | 5/2002 | Armistead et al. |
| 2002/0065270 | A1 | 5/2002 | Moriarty et al. |
| 2003/0064982 | A1 | 4/2003 | Davies et al. |
| 2003/0069248 | A1 | 4/2003 | Chakravarty et al. |
| 2003/0096813 | A1 | 5/2003 | Cao et al. |
| 2003/0105090 | A1 | 6/2003 | Bebbington et al. |
| 2003/0199526 | A1 | 10/2003 | Choquette et al. |
| 2003/0207873 | A1 | 11/2003 | Harrington |
| 2004/0009981 | A1 | 1/2004 | Bebbington et al. |
| 2004/0097531 | A1 | 5/2004 | Ledeboer et al. |
| 2004/0157893 | A1 | 8/2004 | Bebbington et al. |
| 2004/0167141 | A1 | 8/2004 | Bebbington et al. |
| 2004/0214814 | A1 | 10/2004 | Bebbington et al. |
| 2005/0038023 | A1 | 2/2005 | Bebbington et al. |
| 2005/0234059 | A1 | 10/2005 | Hale et al. |
| 2006/0270660 | A1 | 11/2006 | Charrier et al. |

FOREIGN PATENT DOCUMENTS

| | | |
|---|---|---|
| EP | 0136976 | 4/1985 |
| EP | 0302312 A2 | 2/1989 |
| GB | 2 052 487 A | 1/1981 |
| JP | 06-065237 | 3/1994 |
| JP | 10-130150 | 5/1998 |
| JP | 2000-026421 | 1/2000 |
| WO | WO 93/22681 | 11/1993 |
| WO | WO 95/09851 | 4/1995 |
| WO | WO 95/15758 | 6/1995 |
| WO | WO 96/14843 | 5/1996 |
| WO | WO 97/09325 | 3/1997 |
| WO | WO 97/19065 | 5/1997 |
| WO | WO 98/02434 | 1/1998 |
| WO | WO 98/11095 | 3/1998 |
| WO | WO 98/14450 | 4/1998 |
| WO | WO 98/16502 | 4/1998 |
| WO | WO 98/38171 | 9/1998 |
| WO | WO 99/18781 | 4/1999 |
| WO | WO 99/41253 | 8/1999 |
| WO | WO 99/47154 | 9/1999 |
| WO | WO 99/62518 | 12/1999 |
| WO | WO 99/65897 | 12/1999 |
| WO | WO 00/12497 | 3/2000 |
| WO | WO 00/21955 | 4/2000 |
| WO | WO 00/38675 | 7/2000 |
| WO | WO 00/39101 | 7/2000 |
| WO | WO 00/42029 | 7/2000 |
| WO | WO 00/59509 | 10/2000 |
| WO | WO 00/78757 | 12/2000 |
| WO | WO 01/12621 | 2/2001 |
| WO | WO 01/25220 | 4/2001 |
| WO | WO 01/39777 | 6/2001 |
| WO | WO 01/40215 | 6/2001 |
| WO | WO 01/44242 | 6/2001 |
| WO | WO 01/47879 | 7/2001 |
| WO | WO 01/47897 | 7/2001 |
| WO | WO 01/60816 | 8/2001 |
| WO | WO 01/64655 | 9/2001 |
| WO | WO 01/74768 | 10/2001 |
| WO | WO 01/79198 | 10/2001 |
| WO | WO 02/08244 | 1/2002 |
| WO | WO 02/18346 | 3/2002 |
| WO | WO 02/22601 | 3/2002 |
| WO | WO 02/22602 | 3/2002 |
| WO | WO 02/22603 | 3/2002 |
| WO | WO 02/22604 | 3/2002 |
| WO | WO 02/22605 | 3/2002 |
| WO | WO 02/22606 | 3/2002 |
| WO | WO 02/22607 | 3/2002 |
| WO | WO 02/22608 | 3/2002 |
| WO | WO 02/24667 | 3/2002 |
| WO | WO 02/47690 | 6/2002 |
| WO | WO 02/50065 | 6/2002 |
| WO | WO 02/50066 | 6/2002 |
| WO | WO 02/057259 | 7/2002 |
| WO | WO 02/059111 | 8/2002 |
| WO | WO 02/059112 | 8/2002 |
| WO | WO 02/062789 | 8/2002 |
| WO | WO 02/066461 | 8/2002 |
| WO | WO 02/068415 | 9/2002 |
| WO | WO 02/079197 | 10/2002 |
| WO | WO 2004/000833 | 12/2003 |
| WO | WO 2004/013140 | 2/2004 |

OTHER PUBLICATIONS

Anderson, Neil G. "Requirements for integration of signals from two distinct phosphorylation pathways for activation of MAP kinase." Nature, 343, 651-653 (1990).

Anonymous, "Vertex Inhibitors of Aurora-2, glycogen synthase kinase-3 and Src Kinase", Expert Opin. Ther. Patents, 14(3): 439-443 (2004).

Baig, G.U. et al., "Triazines and Related Products. Part 28' Conversion of 3-Aryl-l-(2-cyanophenyl) triazenes into 3-Arylquinazolin-4(3H)-ones with Formamide" J. Chem. Soc. Perkin Trans. I, 2765-2766 (1984).

Baig, Ghouse Unissa et al. "Triazines and related products. Part 27: Therrmolysis of 4-anilino-1,2,3-benzotriazines," *J. Chem., Soc., Perkin Trans*. 1(5): 999-1003 (1984).

Banker, G.S. et al., "Modern Pharmaceutics", 3rd ed., Marcel Dekker, New York 1996, pp. 451 & 596.

Biagi, G. et al., "Synthesis of 4,6-Disubstituted and 4,5,6-Trisubstituted-2-Phenly-pyrimidines and their Affinity Towards A1 Adenosine Receptors", IL Farmaco., 52(1), 61-65 (1997).

Biscardi, J.S. et al., "c-Src, Receptor Tyrosine Kinases, and Human Cancer", Adv. Cancer Res., 76, 61 (1999).

Bischoff, J.R., et al., "A homologue of *Drosophila aurora* kinase is oncogenic and amplified in human colorectal cancers", The EMBO Journal, 17(11): 3052-3065 (1998).

Bishoff, J.R., et al., "The Auroa/Ipl1p kinase family: regulators of chromosome segregation and cytokinesis", Cell Biology, 9, 454-459 (1999).

Bjorbaek, C. et al, "Divergent Functional Roles for p90rsk Kinase Domains", J. Biol. Chem., 270(32), 18848-18552 (1995).

Bokemeyer, D. et al., "Multiple intracellular MAP kinase signaling cascades", Kidney Int., 49, 1187-1198 (1996).

Bolen, J.B. et al., "Activation of pp60c-src protein kinase activity in human colon carcinoma", PNAS, 84, 2251-2255 (1987).

Boschelli et al., "Small molecule inhibitors of Src family kinases", Drugs of the Future, 25(7): 717-736 (2000).

Brownlees, J. et al., "Tau phosphorylation in transgenic mice expressing glycogen synthase kinase-3beta transgenes", Neuroreport., 8(15), 3251-5 (1997).

Brunswick, D.J. et al., "Cyclic Amidines. Part XXII. Novel Isomerism of Disubstituted Tricycioquinazolines and Molecular Orientations in Carcinogenesis", J. Chem. Soc. (C), 2641-2647 (1970).

Campbell, S.F. et al., "2,4-Diamino-6,7-dimethoxyquinazolines. 3.2-(4-Heterocyclylpiperazin-l-yl) Derivatives as α1-Adrenoceptor Antagonists and Antihypertensive Agents," J. Med. Chem., 30, 1794-1798 (1987).

CAPLUS listing Accession No. 1994:292136, Nakajima, Y. et al., "Pyrazoles agricultural and horticultural bactericides," JP 06065237 (1994).

Casanova, B. et al., "Revisión crítica de la patogenia actual de la esclerosis múltiple y futuras direcciones posibles," Rev. Neurol., 28 (9): 909-915 (1999).

Chalmers, D.T. et al., "Corticotrophin-releasing factor receptors: from molecular biology to drug design," TiPS, 17, 769-776 (2001).

Charpiot, B. et al., "Quinazolines: Combined type 3 and 4 phosphodiesterase inhibitors", Bioorg. Med. Chem. Lett., 8(20), 2891-2896 (1998).

Chen, R.H. et al., "Phosphorylation of the c-Fos transrepression domain by mitogen-activated protein kinase and 90-kDa ribosomal S6 kinase", Proc. Natl. Acad. Sci. USA, 90, 10952-10956 (1993).

Cline, G.W. et al., "Effects of a Novel Glycogen Synthase Kinase-3 Inhibitor on Insulin-Stimulated Glucose Metabolism in Zucker Diabetic Fatty (fa/fa) Rats," Diabetes, 51, 2903-2910 (2002).

Coghlan, M.P. et al., "Selective small molecule inhibitors of glycogen synthase kinase-3 modulate glycogen metabolism and gene transcription", Chemistry & Biology,7, 793-803 2000.

Cohen, P. et al., "The renaissance of GSK3," Nat. Rev. Mol. Cell Biol., 2, 769-776 (2001).

Cohen, P., "Dissection of the Protein Phophorylation Cascades Involved in Insulin and Growth Factor Action", Biochem. Soc. Trans., 21, 555-567 (1993).

Coleman, R.A., "The Biological Evaluation of New Compounds" in Medicinal Chemistry: Principles and Practice, King, Frank D. ed, Royal Society of Chemistry, 53-66 (1994).

Crespo, M.I. et al., "Design, Synthesis, and Biological Activities of New Thieno[3,2-d]pyrimidines as Selective Type 4 Phosphodiesterase Inhibitors", J. Med. Chem., 41 (21), 4021-4035 (1998).

Crews, C.M. et al., "The Primary Structure of MEK, a Protein Kinase That Phosphorylates the ERK Gene Product", Science, 228, 478-480 (1992).

Cross, D.A.E. et al., "The inhibition of glycogen synthase kinase-3 by insulin or insulin-like growth factor 1 in the rat skeletal muscle cell line L6 is blocked by wortmannin, but not by rapamycin: evidence that wortmannin blocks activation of the mitogen-activated protein kinase pathway in L6 cells between Ras and Raf", Biochem J., 303: 21-26 (1994).

Curd, F.H.S. et al, "Synthetic antimalarials, Part XVII. Some aminoalkylaminoquinoline derivatives", J. Chem. Soc., 899-909 (1947).

D'Atri, G. et al., "Novel pyrimidine and 1,3,5-triazine hypolipemic agents", J. Med. Chem. 27(12), 1621-1629 (1984).

Damasio, A.R., "Alzheimer's Disease and Related Dementias," in Cecil Textbook of Medicine, 20th ed., 2: 1992-1996 (1996).

Douglas, et al., "Introduction to Viral Disease" in Cecil Textbook of Medicine, 20th Ed., vol. 2, 1739-1749 (1996).

Eldar-Finkelman, H. et al., "Challenges and opportunities with glycogen synthase kinase-3 inhibitors for insulin resistance and Type2 diabetes treatment," Expert Opinion on Investigational Drugs, 12(9): 1511-1519 (2003).

Fedorynski, M. et al., "Synthesis of 1-Arycyclopropanecarbonitriles under Phase-transfer Catalytic Conditions", Org. Prep. Proced. Int., 27(3), 355-359 (1995).

Fischer, P.M. et al., "Inhibitors of Cyclin-Dependent Kinases as Anti-Cancer Therapeutics", Current Med. Chem., 7, 1213-1245 (2000).

Fisher A., "Therapeutic Strategies in Alzheimer's Disease: M1 Muscarinic Agonists," Jpn. J. Pharmacol., 84(2):101-12 (2000).

Fox T. et al., "A single amino acid substitution makes ERK2 susceptible to pyridinyl imidazole inhibitors of p38 MAP kinase", Protein Sci., 7: 2249-2255 (1998).

Frame, M.C., "Src in cancer: deregulation and consequences for cell behaviour," Biochimica et Biophysica Acta., 1602, 114-130 (2002).

Frampton, J.E. et al., "Pentoxifylline (Oxpentifylline)—A Review of its Therapeutic Efficacy in the Management of Peripheral Vascular and Cerebrovascular Disorder," Drugs & Aging, 7(6): 480-503 (1995).

Frey, R.S. et al., "Involvment of Extracellular Signal-regulated Kinase 2 and Stress-activated Protein Kinase/Jun N-Terminal Kinase Activation by Transforming Growth Factor β in the Negative Growth Control of Breast Cancer Cells", Cancer Res., 57, 628-633 (1997).

Fry, D.W. et al,. "Inhibitors of cyclin-dependent kinases as therapeutic agents for the treatment of cancer", Current Opin. Oncol. Endoc. & Metab. Investig., 2-40-59 (2000).

Ganellin, C.R., "Past Approaches to Discovering New Drugs as Medicines" in Medicinal Chemistry, Principles and Practices. King, Frank D. ed, Royal Society of Chemistry, 189-205 (1994).

Garigipati, R.S., "An efficient conversion of nitriles to amidines," Tethrahedron Lett., 31(14), 1969-1972 (1990).

Gershon, H. et al., "Pyrimidines. 7. A Study of the Chlorination of Pyrimidines with Phosphorus Oxychloride in the Presence of N,N-Dimethylaniline", J. Heterocyclic Chem., 21, 1161-1167 (1984).

Glossary of Class Names of Organic Compounds and Reactive Intermediate Based on Structure found from http://www.chem.qmul.ac.uk/iupac/class/index.html (last visited on Nov. 18, 2007).

Gnecco, D. et al., "An Improved Preparation of 1-Methyl-4-Cyano-4-phenylpiperidine", Org. Prep. Proced. Int., 18(4), 478-480 (1996).

Hamdane, M. et al., "Pin 1—A Therapeutic Target in Alzheimer Neurodegeneration," J. Mol. Neurosci., 19(3): 275-87 (2002).

Haq, S. et al., "Glycogen Synthase Kinase-3β Is a Negative Regulator of Cardiomyocyte Hypertrophy", J. Cell Biol., 151(1), 117-129 (2000).

Hardt, S.E. et al., "Glycogen Synthase Kinase-3β—A Novel Regulator of Cardiac Hypertrophy and Development," Circulation Research, 90: 1055-1063 (2002).

Harrington, E.A. et al., "VX-680, a potent and selective small-molecule inhibitor of the Aurora kinases, suppresses tumor growth in vivo," Nat. Med., 10(3): 262-267 (2004).

Haworth, R.D. et al., "Synthetic antimalarials. Part XXVII. Some derivatives of phthalazine, quinoxaline, and isoquinoline", J. Chem. Soc., 777-782 (1948).

Heaney, F., et al., "Pyrimidine annelated heterocycles-synthesis and cycloaddition of the first pyrimido[1,4]diazepine N-oxides," J. Chem. Soc., Perkin Trans., 1:622-632 (2001).

Henriksen, E.J. et al., "Modulation of muscle insulin resistance by selective inhibition of GSK-3 in Zucker diabetic fatty rats," Am. J. Physiol. Endocrinol. Metab., 284: E892-E900 (2003).

Heutink, P., "Untangling tau-related dementia", Hum. Mol. Genet., 9(6): 979-986 (2000).

Ife, R.J. et al., "Reversible Inhibitors of the Gastric (H+/K+)-ATPase. 5. Substituted 2,4-Diaminoquinazolines and Thienopyrimidines", J. Med. Chem., 38(14): 2763-2773 (1995).

IUPAC Compendium of Chemical Terminology on a definition of "aliphatic compounds" found from http://www.chemsoc.org/chembytes/goldbook/index.htm (last visited on Nov. 18, 2007).

Ivashchenko A. V. et al., "Synethsis and Study of Heteroaromatic Ligands Containing a Pyrimidine Ring", Khim. Geterotsikl. Soedin., (12), 1673-7, (1980).

Jambhekar, S.S., "Biopharmaceutical Properties of Drug Substances" in Principles of Medicinal Chemistry, 4th ed., 12-24, (1995).

Jeffery, J.E. et al., "Synthesis of sibutramine, a novel cyclobutylalkylamine useful in the treatment of obesity, and its major human metabolites", J. Chem. Soc., Perkin Trans. 1, 21, 2583-2589 (1996).

Katzung, Bertram G., Basic and Clinical Pharmacology, 7th Edition, 1998, pp. 881-884.

Kelarev, V.I. et al., "Synthesis of amino derivatives of 1,3,5-triazine containing 1,3-4-thiadiazole fragments," Izvestiya Vysshikh Uchebnkh Zavedenii, Khimiya I Khimicheskaya Tekhnologiya, 40(5): 27-32 (1997).

Kim, L. et al., "GSK3, a master switch regulating cell-fate specification and tumorigenesis," Current Opinion in Genetics & Development, 10:508-514 (2000).

Kim, Y.Z. et al., "Synthesis and Antimicrobial Activity of Novel [(3-Aminopyrimidiniumyl)thio]methyl Cephalosporins", J. Med. Chem., 37(22); 3828-3833 (1994).

Kimura, M. et al., "Cell Cycle-dependent Expression and Centrosome Localization of a Third Human Aurora/Ipl1-related Protein Kinase AIK3", J. Biol. Chem., 274(11), 7334-7340 (1999).

Klein, P.S. et al., "A molecular mechanism for the effect of lithium on development", PNAS, 93: 8455-8459 (1996).

Layzer, R.B.., "Section Five—Degenerative Diseases of the Nervous System" in Cecil Textbook of Medicine, 20th ed., 2: 2050-2057 (1996).

Lee, S.J. et al., "Discovery of Potent Cyclic GMP Phosphodiesterase Inhibitors. 2-Pyridyl- and 2-Imidazolylquinazolines Possessing Cyclic GMP Phosphodiesterase and Thromboxane Synthesis Inhibitory Activities," J. Med. Chem., 38 (18): 3547-3557 (1995).

Lovestone, S. et al., "Alzheimer's disease-like phosphorylation of the microtubule-associated protein tau by synthases kinase-3 in transfected mammalian cells", Curr. Biol., 4(12), 1077-86 (1994).

Lübbers, T. et al., "Design, synthesis, and structure-activity relationship studies of ATP analogues as DNA gyrase inhibitors", Bioorg. Med. Chem. Lett., 10, 8, 821-826 (2000).

Lutz, M.L. et al., "Overexpression and Activation of the Tyrosine Kinase Src in Human Pancreatic Carcimona", Biochem. Biophys. Res. 243, 503-508 (1998).

Lynch, S.A. et al., "Increased Expression of the src Proto-Oncogene in Hairy Cell Leukemia and a Subgroup of B-Cell Lymphomas", Leukemia, 7(9), 1416-1422 (1993).

Lyrer, P., "Neue Ansätze in der Akutbehandlung des zerebrovaskulären Insultes." Schweiz. Med. Woohen Schr., 124(45); 2005-2012 (1994).

Mani, S. et al., "Cyclin-dependent kinase: novel anticancer agents", Exp. Opin. Invest. Drugs., 8, 1849-1870 (2000).

Masaki, T. et al., "pp60c-src Activation in Hepatocellular Carcinoma of Humans and LEC Rats", Hapatology, 27, 1257 (1998).

Massillon, D. et al., "Identification of the glycogenic compound 5-iodotubercidin as a general protein kinase inhibitor", Biochem J., 299: 123-128 (1994).

Medwid, Jeffrey B. et al., "Preparation of triazolo'1, 5-cipyrimidines as potential antiasthma agents," J. Med. Chem., 33(4): 1230-1241 (1990).

Molina, T.J. et al., "Profound block in thymocyte development in mice lacking p56lck", Nature, 357, 161-164 (1992).

Moodie, S.A. et al., "Complexes of Ras-GTP with Raf-1 and Mitogen-Activated Protein Kinase Kinase", Science, 260(5114), 1658-1661 (1993).

Moss, R.A. et al., "Conversion of 'Obstinate' Nitriles to Amidines by Garigipati's Reaction", Tetrahedron Lett., 36(48), 8761-8764 (1995).

Meyers, M.R. et al., "The synthesis and SAR of new 4-(N-alkyl-N-phenyl) amino-6,7-dimenthoxyquinazolines and 4-(N-alkyl-N-phenyl)aminopyrazolo[3,4-d]pyrimidines, inhibitors of CSF-1R tyrosine kinase activity", Bioorg. Med. Chem. Lett., 7, 4, 421-424 (1997).

Nair, M.D., et al., "3-Chloroisocarbostyril & Its Chlorination Products", Indian J. Chem., vol. 5, 467-470 (1967).

Namikawa, Kazuhiko et al., "Akt/Protein Kinase B Prevents Injury-Induced Motoneuron Death and Accelerates Axonal Regeneration." The Journal of Neuroscience, 20(8), 2875-2886 (2000).

Nezu, Y., et al., "Dimethoxypyrimidines as Novel Herbicides. part 1. Synthesis and Herbicidal Activity of Dimethoxyphanoxyphenoxypyrimidines and Analogues," Pestic. Sci., 47(2): 103-113 (1996).

Nezu, Y. et al., "Dimethoxypyrimidines as Novel Herbicides. part 2. Synthesis and Herbicidal Activity of O-Pyrimidinylasalicylates and Analogues", Pestic. Sci., 47(2): 115-124 (1996).

Nigg, E.A., "Mitotic Kinases as Regulators of Cell Division and its Checkpoints," Nat. Rev. Mol. Cell Biol., 2: 21-32 (2001).

Noell, C.W. et al., "Potential Purine Antagonists. XX. The Preparation and Reactions of Some Methylthiopurines", J. Am. Chem Soc., 81(22), 5997-6007 (1959).

Nomenclature found from http://www.cem.msu.edu/~reusch/Virtual Text/nomen1.htm (last visited on Nov. 18, 2007).

Norman, M.H. et al., "Structure-Activity Relationships of a Series of Pyrrolo[3,2-d]pyrimidine Derivatives and Related Compounds as Neuropeptide Y5 Receptor Antagonists", J. Med. Chem., 43(22), 4288-4312 (2000).

Nugent, R.A. et al., "Pyrimidine Thioethers: A Novel Class of HIV-1 Reverse Transcriptase Inhibitors with Activity Against BHAP-Resistant HIV", J. Med. Chem., 41, 3793-3803 (1998).

Okafor, Charles O., "Studies in the Heterocyclic Series. 1,3,9-Triazaphenothiazine Ring System, a New Phenothiazine Ring," J. Org. Chem., 40(19):2753-2755 (1975).

Parnell, E.W., "2-Cyano-4-nitrophenylhydrazine and 3-Amino-5-nitroindazole", J. Chem. Soc., 2363-2365 (1959).

Pei, J. et al., "Distribution Levels and Activity of Glycogen Synthase Kinase-3 in the Alzheimer Disease Brain", J. Neuropathol. Exp. Neurology, 56, 70-78 (1997).

Prasad, G. et al., "18-Crown-6 as a catalyst in the dialkylation of o-nitrophenacyl derivatives", J. Org. Chem., 25, 7188-7190 (1991).

Raingeaud, J. et al., "MMK3- and MMK6-Regulated Gene Expression Is Mediated by p38 Mitogen-Activated Protein Kinase Signal Transduction Pathway", Mol. Cell. Biol., 16, 1247-1255 (1996).

Rogers, E. et al., "The aurora kinase AIR-2 functions in the release of chromosome cohesion in Caenorhabditis elegans meiosis," J. Cell Biol., 157(2): 219-229 (2002).

Rosen, N. et al., "Analysis of pp60c-src Protein Kinase Activity in Human Tumor Cell Lines and Tissues", J.Biol. Chem., 261, 13754-13759 (1986).

Rouse, J. et al., "A Novel Kinase Cascade Triggered by Stress and Heat Shock That Stimulates MAPKAP Kinase-2 and Phosphorylation of the Small Heat Shock Proteins", Cell, 78, 1027-1037 (1994).

Rueeger, H et al., "Design, synthesis and SAR of a series of 2-substituted 4-amino-quinazoline neuropeptide Y Y5 receptor antagonists", Bioorg. Med. Chem. Lett., 10(11), 1175-1180 (2000).

Shikhaliev, K.S. et al., "Heterocyclization of quinazol-2-ylguanidines. 1. Reaction with amino acids", Chem. Heterocycl. Compd., 35 (7), 818-820 (1999).

Simone, J.V., "Oncology: Introduction" in Cecil Textbook in Medicine, 20th ed. vol. 1, 1004-1010 (1996).

Singh, S.P. et al., "Synthesis & Mass Spectra of Some Substituted 2-(2'-Benzazolylamino)pyrimidines", Indian J. Chem. Sect. B, 22(1); 37-42 (1983).

Singhal, N. et al., "Synthesis and Antimalarial Activity of Some New Quinazoline Derivatives", Indian Chem. Soc., 61, 690-693 (1984).

Sivaraman, V.S., et al., "Hyperexpression of Mitogen-activated Protein Kinase in Human Breast Cancer", J. Clin. Invest., 99(7), 1478-1483 (1997).

Soriano, P. et al., "Targeted Disruption of the C-SRC Proto-Oncogene Leads to Osteopetrosis in Mice," Cell, 64: 693-702, (1991).

Staley, C.A. et al., "Decreased Tumorigenicity of a Human Colon Adenocarcinoma Cell Line by an Antisense Expression Vector Specific for c-Src", Cell Growth Diff., 8, 269-274 (1997).

Suzuki, S. et al., "Application of electrogenerated triphenylmethyl anion as a base for alkylation of arylacetic esters and arylacetonitriles and isomerization of allylbenzenes", Can. J. Chem., 72(2): 357-361 (1994).

Takashima, K. et al., "Tau Protein Kinase I is Essential for Amyloid β-Protein-Induced Neurotoxicity", PNAS 90, 7789-7793 (1993).

Takayanagi, H. et al., "Suppression of arthritic bone destruction by adenovirus-mediated csk gene transfer to synoviocytes and osteoclasts", J. Clin. Invest., 104, 137-146 (1999).

Talamonti, M.S. et al., "Increase in activity and level of pp60c-src in progressive stages of human colorectal cancer", J Clin Invest., 91(1): 53-60 (1993).

Tanaka, T.U. et al., "Evidence that the Ipl1-Sli15 (Aurora Kinase-INCENP) Complex Promotes Chromosome Bi-orientation by Altering Kinetochore-Spindle Pole Connections," Cell, 108, 317-329 (2002).

Tanji, K. et al., "Purines. X. Reactivities of Methyl Groups on 9-Phenylpurines : Condensation with an Aldehyde or an Ester, and Oxidation with Selenium Dioxide", Chem. Phar. Bull., 40 (1), 227-229 (1992).

The Condensed Chemical Dictionary, Sixth Edition by Arthur and Elizabeth Rose, 38 (1961).

Ti, J. et al., "Anticandidal activity of pyrimidine-peptide conjugates", J. Med. Chem., 23(8), 913-918 (1980).

Toriyabe, Keiji et al: "Preparation of sulfur-containing arylthiazoles and insecticides", Chemica Abstracts, 132(8):93314 (2000).

Traxler P. et al., "Use of a pharmacophore model for the design of EGF-R Tyrosine Kinase Inhibitors: 4-(Phenylamino)Pyrazolo[3,4-d]pyrimidines," Journal of Medicinal Chemistry, 40(22): 3601-3616 (1997).

Venugopalan, B. et al., "Synthesis and antimalarial activity of pyrido[3,2-f]quinozalines and their N-oxides", Indian J. Chem. Sect. B, 34, 9, 778-790 (1995).

Wagman, A.S. et al, "Discovery and Development of GSK3 Inhibitors for the Treatment of Type 2 Diabetes", Current Pharmaceutical Design, 1, 1105-1137 (2004).

Warner, S.L. et al, "Targeting Aurora-2 Kinase in Cancer", Mol. Cancer Thera., 2, 589-585, 2003.

Whelchel, A. et al., "Inhibition of ERK Activation Attenuates Endothelin-stimulated Airway Smooth Muscle Cell Proliferation", Am. J. Respir. Cell Mol. Biol., 16, 589-596 (1997).

Weiner, J.R., "Decreased Src Tyrosine Kinase Activity Inhibits Malignant Human Ovarian Cancer Tumor Growth in a Nude Mouse Model", Clin. Cancer Res., 5, 2164-2170 (1999).

Wolft, Manfred E., "Burger's Medicinal Chemistry, 5th ed., Part 1" John Wiley & Sons, 1995, pp. 975-977.

Yuan, Z.Q. et al., "Frequent activation of AKT2 and induction of apoptosis by inhibition of phosphoinositide-3-OH kinase/Akt pathway in human ovarian cancer", Oncogene, 19, 2324-2330 (2000).

Zhang, Z. et al., "Destabilization of β-catenin by mutations in presenilin-1 potentiates neuronal apoptosis", Nature, 395, 698-702 (1998).

* cited by examiner

AMINOPYRIMIDINES USEFUL AS KINASE INHIBITORS

CROSS REFERENCE TO RELATED APPLICATIONS

This present application claims benefit, under 35 U.S.C. §119, to U.S. Provisional Application Nos. 60/732,951, filed Nov. 3, 2005, and 60/733,557, filed Nov. 4, 2005, the entire disclosures of each of which are incorporated herein by reference.

TECHNICAL FIELD OF THE INVENTION

The present invention relates to compounds useful as inhibitors of Aurora protein kinases. The invention also relates to pharmaceutically acceptable compositions comprising the compounds of the invention, methods of using the compounds and compositions in the treatment of various disorders, and processes for preparing the compounds.

BACKGROUND OF THE INVENTION

The Aurora proteins are a family of three related serine/threonine kinases (termed Aurora-A, -B and -C) that are essential for progression through the mitotic phase of cell cycle. Specifically Aurora-A plays a crucial role in centrosome maturation and segregation, formation of the mitotic spindle and faithful segregation of chromosomes. Aurora-B is a chromosomal passenger protein that plays a central role in regulating the alignment of chromosomes on the meta-phase plate, the spindle assembly checkpoint and for the correct completion of cytokinesis.

Overexpression of Aurora-A, -B or -C has been observed in a range of human cancers including colorectal, ovarian, gastric and invasive duct adenocarcinomas.

A number of studies have now demonstrated that depletion or inhibition of Aurora-A or -B in human cancer cell lines by siRNA, dominant negative antibodies or neutralizing antibodies disrupts progression through mitosis with accumulation of cells with 4N DNA, and in some cases this is followed by endoreduplication and cell death.

The Aurora kinases are especially attractive targets due to their association with numerous human cancers and the roles they play in the proliferation of these cancer cells. It would be desirable to have an Aurora kinase inhibitor with favorable drug-like properties, such as the ability to inhibit cell proliferation. Accordingly, there is a need for compounds that inhibit Aurora kinases and also exhibit favorable drug-like properties.

SUMMARY OF THE INVENTION

This invention provides compounds and pharmaceutically acceptable compositions thereof that are useful as inhibitors of Aurora protein kinases. These compounds are represented by formula I:

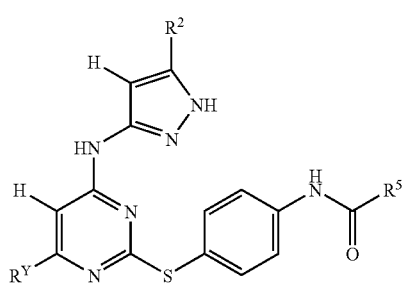

I or a pharmaceutically acceptable salt thereof, wherein the variables are as defined herein.

These compounds and pharmaceutically acceptable compositions thereof are useful for inhibiting kinases in vitro, in vivo, and ex vivo. Such uses include treating or preventing myeloproliferative disorders and proliferative disorders such as melanoma, myeloma, leukemia, lymphoma, neuroblastoma, and cancer. Other uses include the study of kinases in biological and pathological phenomena; the study of intracellular signal transduction pathways mediated by such kinases; and the comparative evaluation of new kinase inhibitors.

DETAILED DESCRIPTION OF THE INVENTION

The present invention provides a compound of formula I:

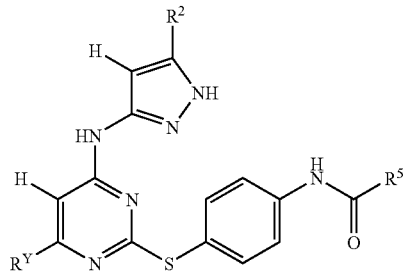

I or a pharmaceutically acceptable salt thereof, wherein:

$R^2$ is $C_{1-3}$ alkyl or cyclopropyl;

$R^5$ is $CH_2CH_3$, $CH_2CF_3$, $CH_2CH_2CF_3$,

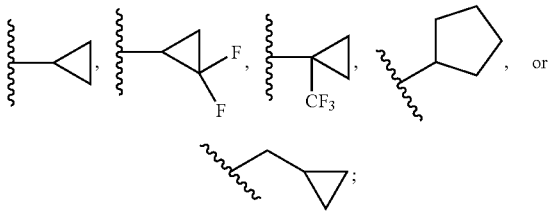

, or

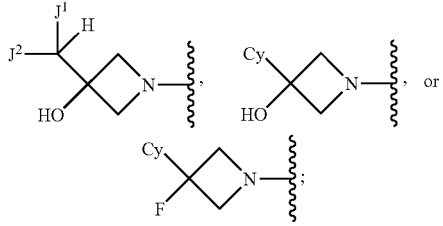

$R^Y$ is

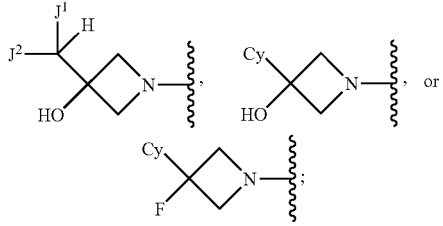

, or $J^1$ is H or $CH_3$;

$J^2$ is $C_{1-4}$ alkyl; and

Cy is $C_{3-5}$ cycloalkyl.

In some aspects of this invention, $R^5$ is selected from $CH_2CF_3$, $CH_2CH_2CF_3$,

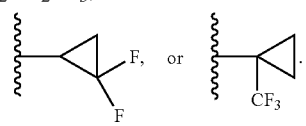

In other embodiments, $R^5$ is selected from $CH_2CF_3$ or
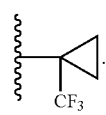
In yet other embodiments, $R^5$ is $CH_2CF_3$.
In other aspects of this invention, $R^Y$ is
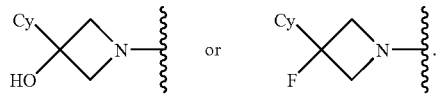
In some embodiments, $R^Y$ is
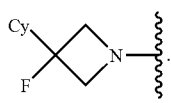
In some embodiments, Cy is cyclopropyl.
In other aspects of this invention, $R^2$ is methyl.
One aspect provides a compound selected from Table 1 (or a pharmaceutically acceptable salt thereof):
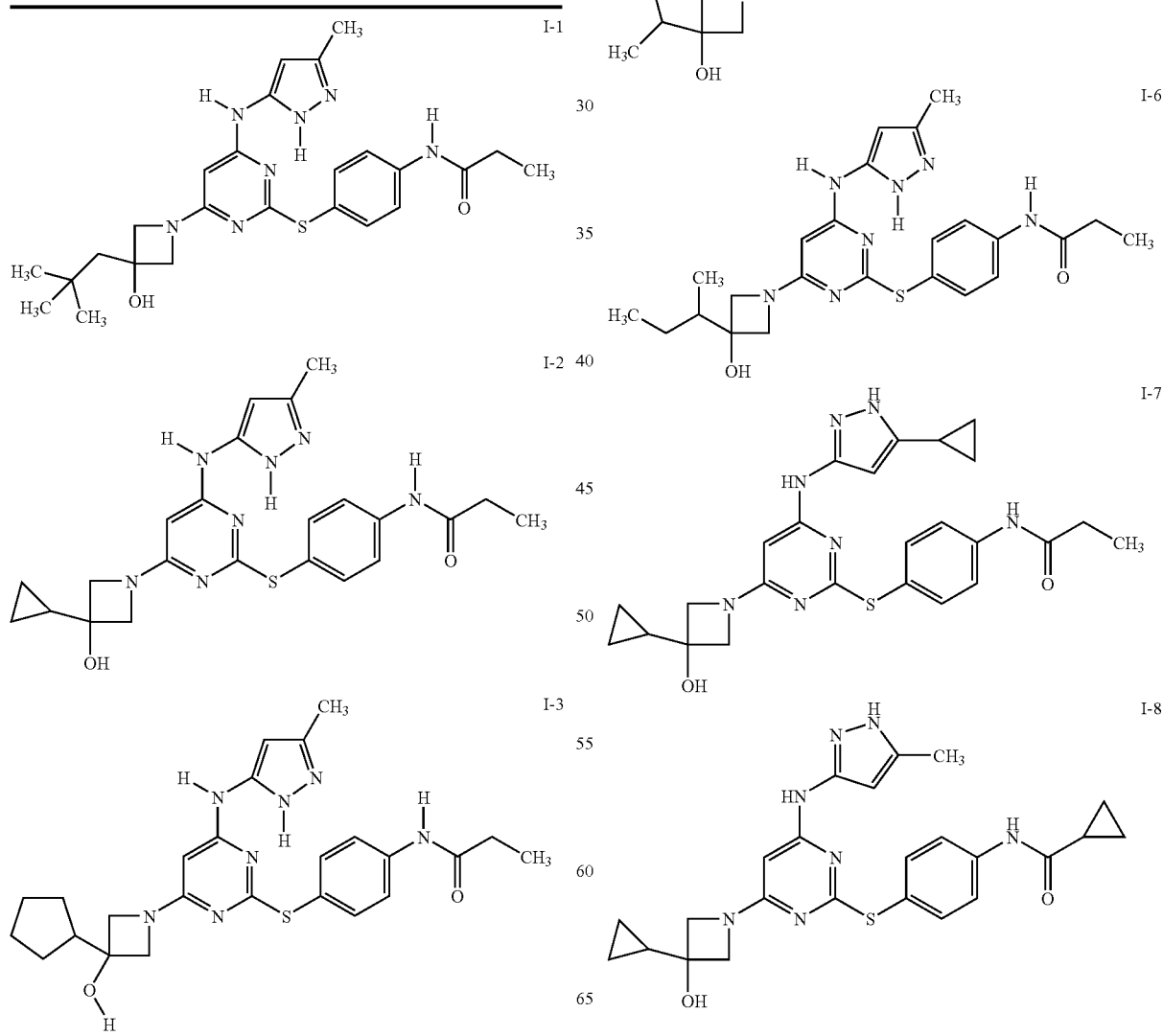

-continued
I-9
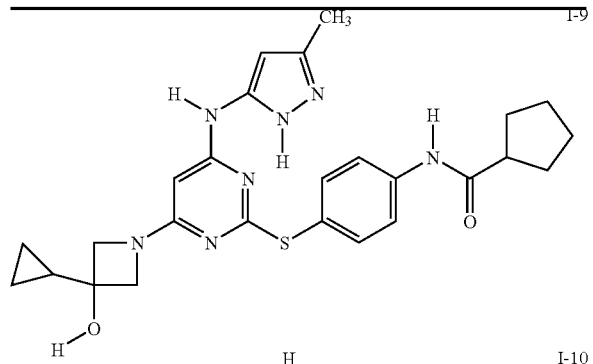
I-10
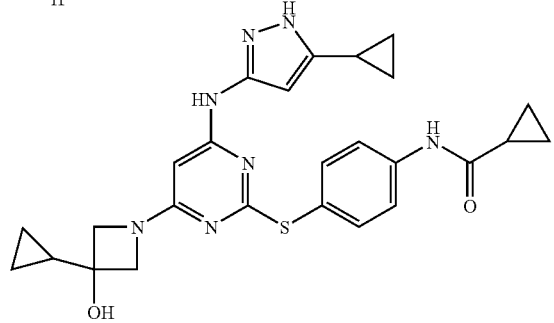
I-11
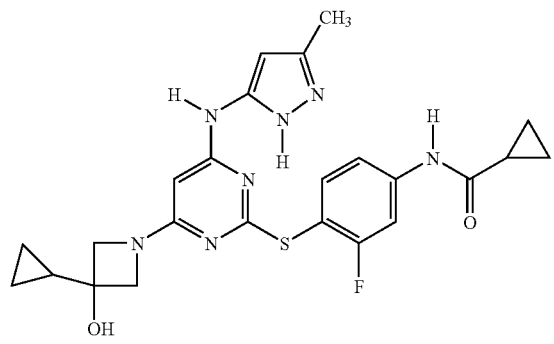
I-12
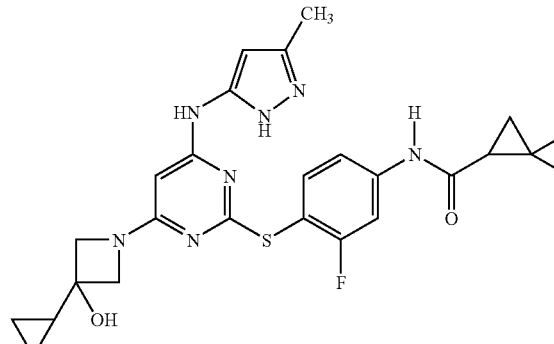
I-13
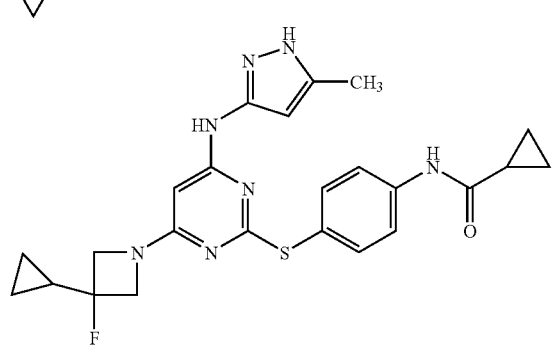
-continued
I-14
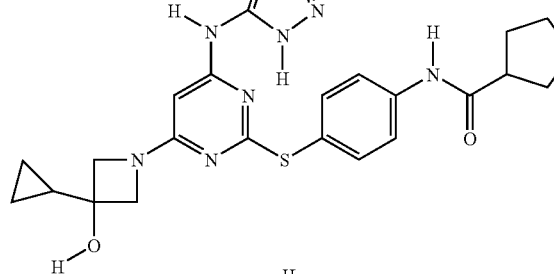
I-15
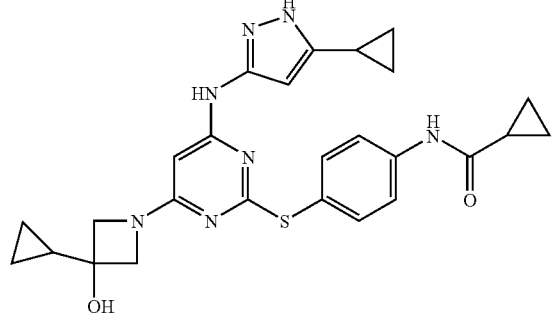
I-16
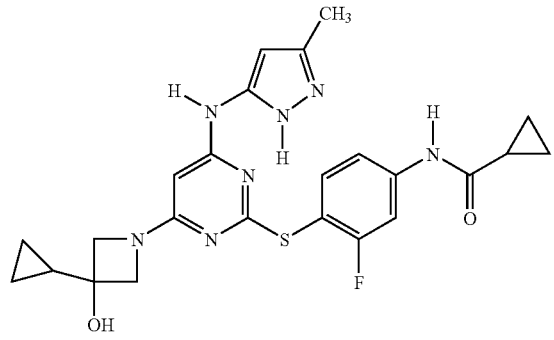
I-17
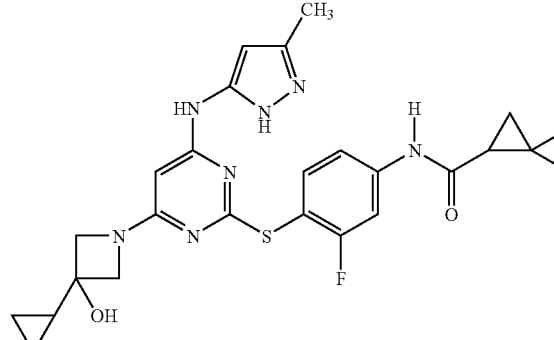
I-18
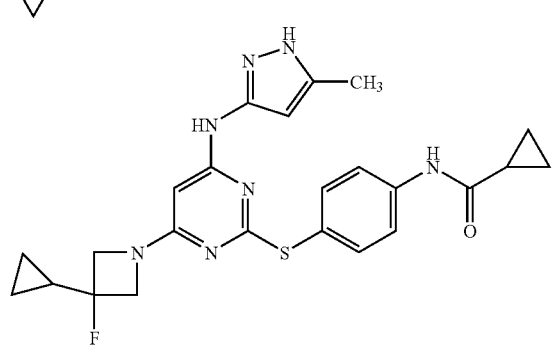

-continued

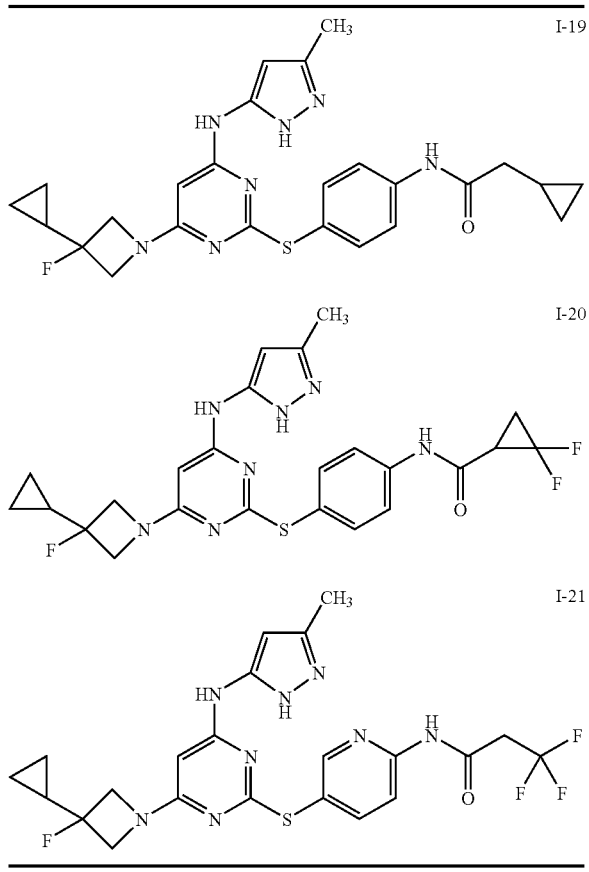

For purposes of this invention, the chemical elements are identified in accordance with the Periodic Table of the Elements, CAS version, Handbook of Chemistry and Physics, 75th Ed. Additionally, general principles of organic chemistry are described in texts known to those of ordinary skill in the art, including, for example, "Organic Chemistry", Thomas Sorrell, University Science Books, Sausalito: 1999, and "March's Advanced Organic Chemistry", 5th Ed., Ed.: Smith, M. B. and March, J., John Wiley & Sons, New York: 2001, the entire contents of which are hereby incorporated by reference.

As described herein, a specified number range of atoms includes any integer therein. For example, a group having from 1-4 atoms could have 1, 2, 3, or 4 atoms.

As described herein, compounds of the invention may optionally be substituted with one or more substituents, such as are illustrated generally above, or as exemplified by particular classes, subclasses, and species of the invention. It will be appreciated that the phrase "optionally substituted" is used interchangeably with the phrase "substituted or unsubstituted." In general, the term "substituted", whether preceded by the term "optionally" or not, refers to the replacement of hydrogen radicals in a given structure with the radical of a specified substituent. Unless otherwise indicated, an optionally substituted group may have a substituent at each substitutable position of the group, and when more than one position in any given structure may be substituted with more than one substituent selected from a specified group, the substituent may be either the same or different at every position. Combinations of substituents envisioned by this invention are preferably those that result in the formation of stable or chemically feasible compounds.

The term "stable", as used herein, refers to compounds that are not substantially altered when subjected to conditions to allow for their production, detection, and preferably their recovery, purification, and use for one or more of the purposes disclosed herein. In some embodiments, a stable compound or chemically feasible compound is one that is not substantially altered when kept at a temperature of 40° C. or less, in the absence of moisture or other chemically reactive conditions, for at least a week.

The term "alkyl" as used herein, means an unbranched or branched, straight-chain hydrocarbon that is completely saturated and has a single point of attachment to the rest of the molecule. Specific examples of alkyl groups include, but are not limited to, methyl, ethyl, isopropyl, n-propyl, and sec-butyl.

The term "cycloalkyl" refers to a monocyclic hydrocarbon that is completely saturated and has a single point of attachment to the rest of the molecule. Suitable cycloalkyl groups include, but are not limited to, cyclopropyl, cyclobutyl, and cyclopentyl.

The term "unsaturated", as used herein, means that a moiety has one or more units of unsaturation.

The terms "haloalkyl" means an alkyl substituted with one or more halogen atoms. This includes perfluorinated alkyl groups, such as $CF_3$.

The term "halogen" means F, Cl, Br, or I.

The term "protecting group", as used herein, refers to an agent used to temporarily block one or more desired reactive sites in a multifunctional compound. In certain embodiments, a protecting group has one or more, or preferably all, of the following characteristics: a) reacts selectively in good yield to give a protected substrate that is stable to the reactions occurring at one or more of the other reactive sites; and b) is selectively removable in good yield by reagents that do not attack the regenerated functional group. Exemplary protecting groups are detailed in Greene, T. W., Wuts, P. G in "Protective Groups in Organic Synthesis", Third Edition, John Wiley & Sons, New York: 1999, and other editions of this book, the entire contents of which are hereby incorporated by reference. The term "nitrogen protecting group", as used herein, refers to an agents used to temporarily block one or more desired nitrogen reactive sites in a multifunctional compound. Preferred nitrogen protecting groups also possess the characteristics exemplified above, and certain exemplary nitrogen protecting groups are also detailed in Chapter 7 in Greene, T. W., Wuts, P. G in "Protective Groups in Organic Synthesis", Third Edition, John Wiley & Sons, New York: 1999, the entire contents of which are hereby incorporated by reference.

Unless otherwise indicated, structures depicted herein are also meant to include all isomeric (e.g., enantiomeric, diastereomeric, and geometric (or conformational)) forms of the structure; for example, the R and S configurations for each asymmetric center, (Z) and (E) double bond isomers, and (Z) and (E) conformational isomers. Therefore, single stereochemical isomers as well as enantiomeric, diastereomeric, and geometric (or conformational) mixtures of the present compounds are within the scope of the invention.

Unless otherwise indicated, all tautomeric forms of the compounds of the invention are within the scope of the invention. As would be understood by a skilled practitioner, a pyrazole group can be represented in a variety of ways. For example, a structure drawn as

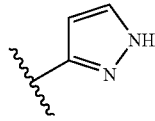

represents other possible tautomers, such as

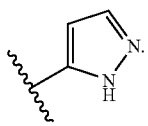

Likewise, a structure drawn as

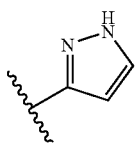

also represents other possible tautomers, such as

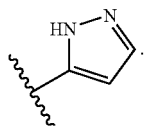

Unless otherwise indicated, a substituent can freely rotate around any rotatable bonds. For example, a substituent drawn as

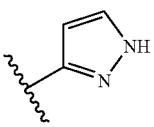

also represents

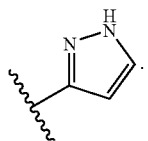

Likewise, a substituent drawn as

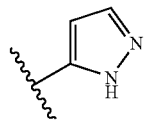

also represents

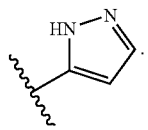

Additionally, unless otherwise indicated, structures depicted herein are also meant to include compounds that differ only in the presence of one or more isotopically enriched atoms. For example, compounds having the present structures except for the replacement of hydrogen by deuterium or tritium, or the replacement of a carbon by a $^{13}C$- or $^{14}C$-enriched carbon are within the scope of this invention. Such compounds are useful, for example, as analytical tools or probes in biological assays.

The compounds of this invention may be prepared in light of the specification using steps generally known to those of ordinary skill in the art. Those compounds may be analyzed by known methods, including but not limited to LCMS (liquid chromatography mass spectrometry) and NMR (nuclear magnetic resonance). It should be understood that the specific conditions shown below are only examples, and are not meant to limit the scope of the conditions that can be used for making compounds of this invention. Instead, this invention also includes conditions that would be apparent to those skilled in that art in light of this specification for making the compounds of this invention. Unless otherwise indicated, all variables in the following schemes are as defined herein.

The following abbreviations are used:
DIPEA is diisopropylethylamine
DMF is dimethylformamide
n-BuOH is n-butanol
t-BuOH is tert-butanol
EtOH is ethanol
MeOH is methanol
EtOAc is ethyl acetate
TFA is trifluoroacetic acid
DMSO is dimethyl sulfoxide
Rt is retention time
DCM is dichloromethane
MeCN is acetonitrile
THF is tetrahydrofuran
TBTU is 2-(1H-Benzotriazole-1-yl)-1,1,3,3-tetramethyluronium tetrafluoroborate
HPLC is high performance liquid chromatography
LCMS liquid chromatography mass spectrometry
$^1H$ NMR is nuclear magnetic resonance General Scheme

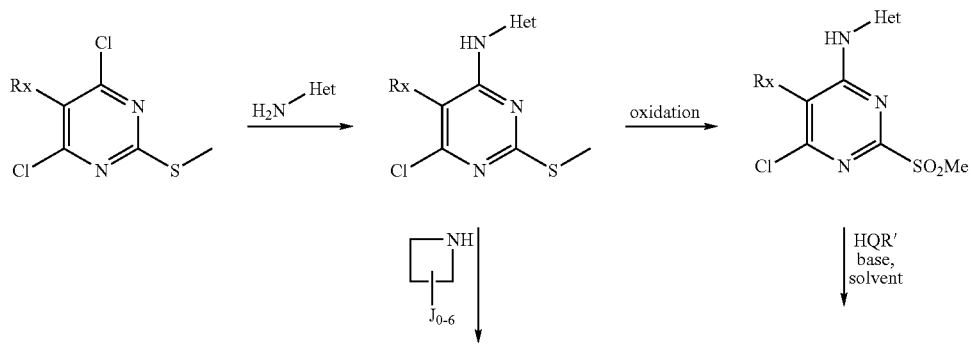

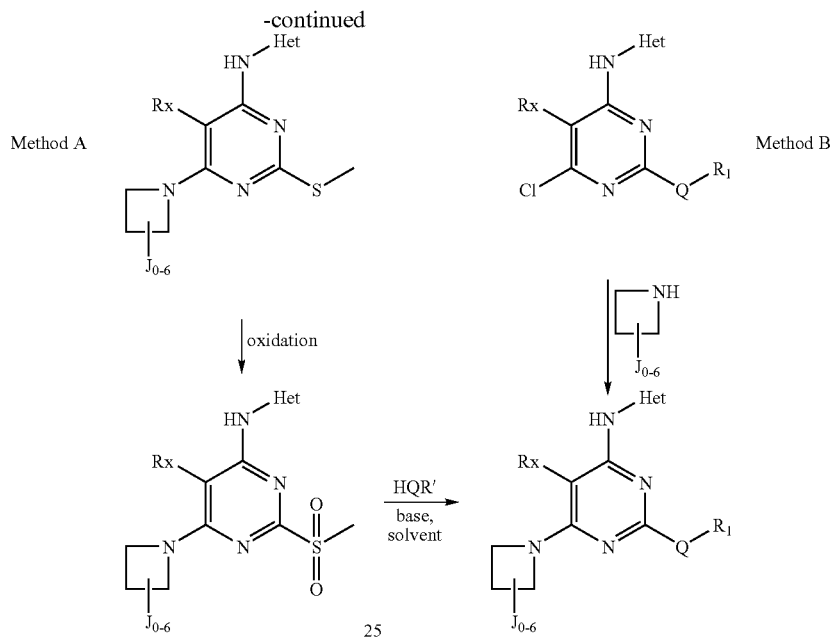

The general scheme above shows some methods of making compounds of this invention.

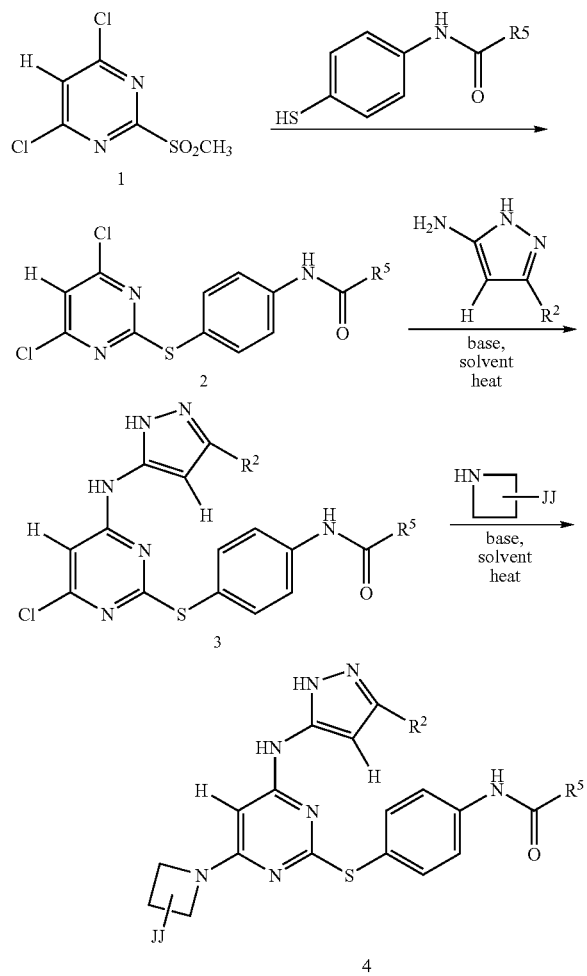

Scheme I above shows a general route for the preparation of compounds of formula 4 (in Scheme I), wherein JJ corresponds to the substitutions on the azetidine as described herein and wherein $R^2$ and $R^5$ are as defined herein. The dichlorinated pyrimidine of formula 1 is combined with HQ-$R^1$ to form a compound of formula 2. In some embodiments, the two compounds are heated in the presence of a suitable solvent (e.g. t-BuOH) for 16 hours. In other embodiments, the two compounds are mixed at 0° C. in the presence of acetonitrile and triethylamine for 1 hour. The compound of formula 2 is then heated in the presence of a suitable solvent (e.g. DMF) and a suitable base (e.g. DIPEA/NaI) with an optionally substituted aminopyrazole to form a compound of formula 3, which is heated in the presence of an azetidine derivative in the presence of a suitable solvent (e.g. n-BuOH) to form a compound of formula 4.

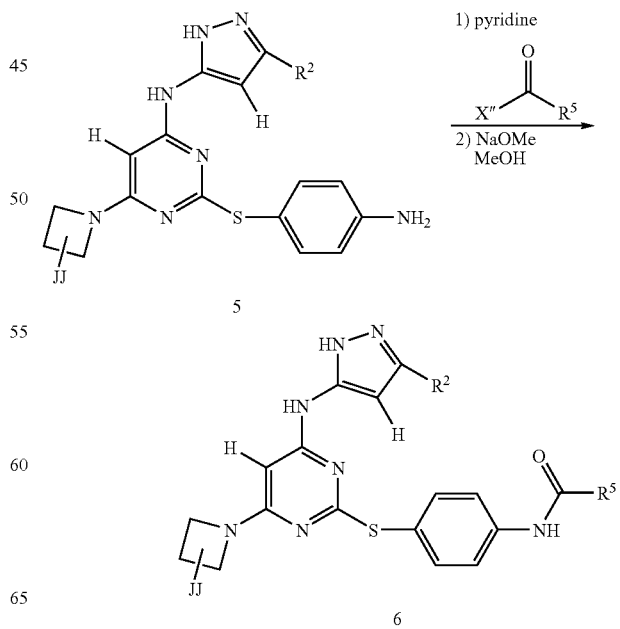

Scheme II above shows a general route for the preparation of compounds of formula 6 (in Scheme II), wherein JJ corresponds to the substitutions on the azetidine as described herein and wherein $R^2$ and $R^5$ are as defined herein. The compound of 5 is combined with a suitable acid chloride (wherein X" is Cl) in the presence of pyridine to form an intermediate compound that, upon mixing in the presence of sodium methoxide and methanol, forms the compound of formula 6. In some embodiments, X" can be OH, in which case a suitable acid coupling reagent is used to couple the acid to the amine. Examples of suitable acid coupling reagents include, but are not limited to, EDC, DCI, and HOBT. Suitable solvents for these coupling reactions include, but are not limited to, THF, $CH_2Cl_2$, and dioxane.

The following schemes depict methods for synthesizing various types of azetidines. Theses azetidines can be used to form compounds of this invention according to the methods described herein.

Scheme A

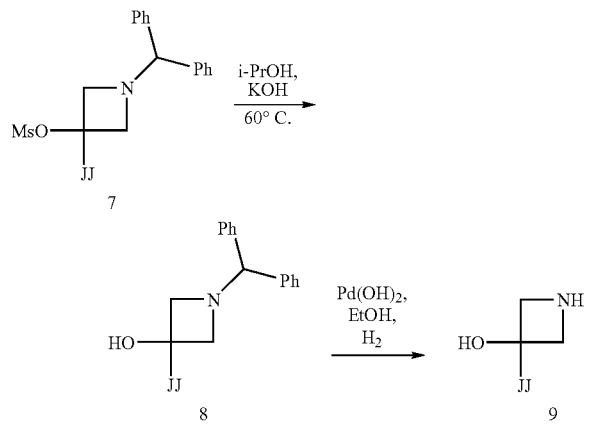

Scheme A above shows a general route for the preparation of OH substituted azetidines wherein JJ is —$CHJ^1J^2$, or Cy.

Scheme B

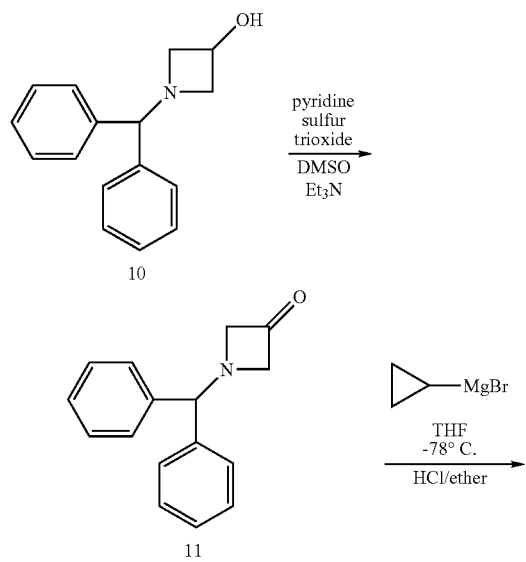

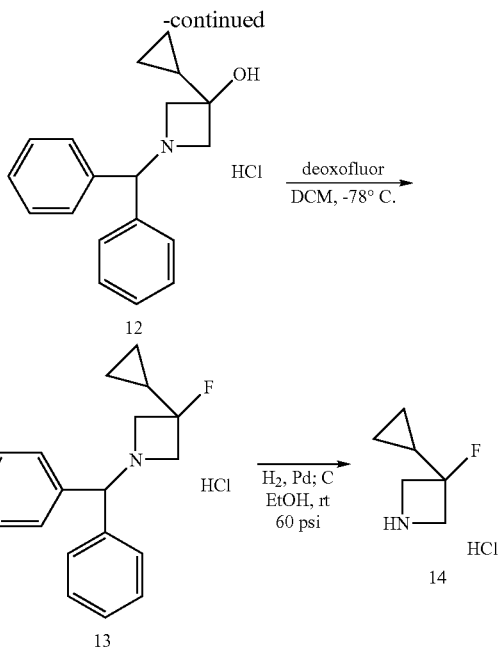

Scheme B depicts a general route for the preparation of cyclopropyl-fluoro-substituted azetidines. Compound 10 is oxidized under suitable conditions to form compound 11, which, under suitable Grignard conditions, is combined with cyclopropyl-MgBr to form the cyclopropyl-substituted azetidine 12. Compound 12 is then fluorinated under suitable fluorination conditions to form 13, which is hydrogenated under Pd/C conditions to form the deprotected free azetidine 14.

Accordingly, this invention relates to processes for making the compounds of this invention.

Methods for evaluating the activity of the compounds of this invention (e.g., kinase assays) are known in the art and are also described in the examples set forth.

The activity of the compounds as protein kinase inhibitors may be assayed in vitro, in vivo or in a cell line. In vitro assays include assays that determine inhibition of either the kinase activity or ATPase activity of the activated kinase. Alternate in vitro assays quantitate the ability of the inhibitor to bind to the protein kinase and may be measured either by radiolabelling the inhibitor prior to binding, isolating the inhibitor/kinase complex and determining the amount of radiolabel bound, or by running a competition experiment where new inhibitors are incubated with the kinase bound to known radioligands.

Another aspect of the invention relates to inhibiting kinase activity in a biological sample, which method comprises contacting said biological sample with a compound of formula I or a composition comprising said compound. The term "biological sample", as used herein, means an in vitro or an ex vivo sample, including, without limitation, cell cultures or extracts thereof; biopsied material obtained from a mammal or extracts thereof; and blood, saliva, urine, feces, semen, tears, or other body fluids or extracts thereof.

Inhibition of kinase activity in a biological sample is useful for a variety of purposes that are known to one of skill in the art. Examples of such purposes include, but are not limited to, blood transfusion, organ-transplantation, biological specimen storage, and biological assays.

Inhibition of kinase activity in a biological sample is also useful for the study of kinases in biological and pathological phenomena; the study of intracellular signal transduction pathways mediated by such kinases; and the comparative evaluation of new kinase inhibitors.

The Aurora protein kinase inhibitors or pharmaceutical salts thereof may be formulated into pharmaceutical compositions for administration to animals or humans. These pharmaceutical compositions, which comprise an amount of the Aurora protein inhibitor effective to treat or prevent an Aurora-mediated condition and a pharmaceutically acceptable carrier, are another embodiment of the present invention.

The term "Aurora-mediated condition" or "Aurora-mediated disease" as used herein means any disease or other deleterious condition in which Aurora (Aurora A, Aurora B, and Aurora C) is known to play a role. Such conditions include, without limitation, cancer, proliferative disorders, and myeloproliferative disorders.

Examples of myeloproliferative disorders include, but are not limited, to, polycythemia vera, thrombocythemia, myeloid metaplasia with myelofibrosis, chronic myelogenous leukaemia (CML), chronic myelomonocytic leukemia, hypereosinophilic syndrome, juvenile myelomonocytic leukemia, and systemic mast cell disease.

The term "cancer" also includes, but is not limited to, the following cancers: epidermoid Oral: buccal cavity, lip, tongue, mouth, pharynx; Cardiac: sarcoma (angiosarcoma, fibrosarcoma, rhabdomyosarcoma, liposarcoma), myxoma, rhabdomyoma, fibroma, lipoma and teratoma; Lung: bronchogenic carcinoma (squamous cell or epidermoid, undifferentiated small cell, undifferentiated large cell, adenocarcinoma), alveolar (bronchiolar) carcinoma, bronchial adenoma, sarcoma, lymphoma, chondromatous hamartoma, mesothelioma; Gastrointestinal: esophagus (squamous cell carcinoma, larynx, adenocarcinoma, leiomyosarcoma, lymphoma), stomach (carcinoma, lymphoma, leiomyosarcoma), pancreas (ductal adenocarcinoma, insulinoma, glucagonoma, gastrinoma, carcinoid tumors, vipoma), small bowel or small intestines (adenocarcinoma, lymphoma, carcinoid tumors, Karposi's sarcoma, leiomyoma, hemangioma, lipoma, neurofibroma, fibroma), large bowel or large intestines (adenocarcinoma, tubular adenoma, villous adenoma, hamartoma, leiomyoma), colon, colon-rectum, colorectal; rectum, Genitourinary tract: kidney (adenocarcinoma, Wilm's tumor [nephroblastoma], lymphoma, leukemia), bladder and urethra (squamous cell carcinoma, transitional cell carcinoma, adenocarcinoma), prostate (adenocarcinoma, sarcoma), testis (seminoma, teratoma, embryonal carcinoma, teratocarcinoma, choriocarcinoma, sarcoma, interstitial cell carcinoma, fibroma, fibroadenoma, adenomatoid tumors, lipoma); Liver: hepatoma (hepatocellular carcinoma), cholangiocarcinoma, hepatoblastoma, angiosarcoma, hepatocellular adenoma, hemangioma, biliary passages; Bone: osteogenic sarcoma (osteosarcoma), fibrosarcoma, malignant fibrous histiocytoma, chondrosarcoma, Ewing's sarcoma, malignant lymphoma (reticulum cell sarcoma), multiple myeloma, malignant giant cell tumor chordoma, osteochronfroma (osteocartilaginous exostoses), benign chondroma, chondroblastoma, chondromyxofibroma, osteoid osteoma and giant cell tumors; Nervous system: skull (osteoma, hemangioma, granuloma, xanthoma, osteitis deformans), meninges (meningioma, meningiosarcoma, gliomatosis), brain (astrocytoma, medulloblastoma, glioma, ependymoma, germinoma [pinealoma], glioblastoma multiform, oligodendroglioma, schwannoma, retinoblastoma, congenital tumors), spinal cord neurofibroma, meningioma, glioma, sarcoma); Gynecological: uterus (endometrial carcinoma), cervix (cervical carcinoma, pre-tumor cervical dysplasia), ovaries (ovarian carcinoma [serous cystadenocarcinoma, mucinous cystadenocarcinoma, unclassified carcinoma], granulosa-thecal cell tumors, Sertoli-Leydig cell tumors, dysgerminoma, malignant teratoma), vulva (squamous cell carcinoma, intraepithelial carcinoma, adenocarcinoma, fibrosarcoma, melanoma), vagina (clear cell carcinoma, squamous cell carcinoma, botryoid sarcoma (embryonal rhabdomyosarcoma), fallopian tubes (carcinoma), breast; Hematologic: blood (myeloid leukemia [acute and chronic], acute lymphoblastic leukemia, chronic lymphocytic leukemia, myeloproliferative diseases, multiple myeloma, myelodysplastic syndrome), Hodgkin's disease, non-Hodgkin's lymphoma [malignant lymphoma] hairy cell; lymphoid disorders; Skin: malignant melanoma, basal cell carcinoma, squamous cell carcinoma, Karposi's sarcoma, keratoacanthoma, moles dysplastic nevi, lipoma, angioma, dermatofibroma, keloids, psoriasis, Thyroid gland: papillary thyroid carcinoma, follicular thyroid carcinoma; medullary thyroid carcinoma, undifferentiated thyroid cancer, multiple endocrine neoplasia type 2A, multiple endocrine neoplasia type 2B, familial medullary thyroid cancer, pheochromocytoma, paraganglioma; and Adrenal glands: neuroblastoma. Thus, the term "cancerous cell" as provided herein, includes a cell afflicted by any one of the above-identified conditions. In some embodiments, the cancer is selected from colorectal, thyroid, or breast cancer.

In some embodiments, the compounds of this invention are useful for treating cancer, such as colorectal, thyroid, breast, and lung cancer; and myeloproliferative disorders, such as polycythemia vera, thrombocythemia, myeloid metaplasia with myelofibrosis, chronic myelogenous leukemia, chronic myelomonocytic leukemia, hypereosinophilic syndrome, juvenile myelomonocytic leukemia, and systemic mast cell disease.

In some embodiments, the compounds of this invention are useful for treating hematopoietic disorders, in particular, acute-myelogenous leukemia (AML), chronic-myelogenous leukemia (CML), acute-promyelocytic leukemia (APL), and acute lymphocytic leukemia (ALL).

In addition to the compounds of this invention, pharmaceutically acceptable derivatives or prodrugs of the compounds of this invention may also be employed in compositions to treat or prevent the above-identified disorders.

A "pharmaceutically acceptable derivative or prodrug" means any pharmaceutically acceptable ester, salt of an ester or other derivative of a compound of this invention which, upon administration to a recipient, is capable of providing, either directly or indirectly, a compound of this invention or an inhibitorily active metabolite or residue thereof. Such derivatives or prodrugs include those that increase the bioavailability of the compounds of this invention when such compounds are administered to a patient (e.g., by allowing an orally administered compound to be more readily absorbed into the blood) or which enhance delivery of the parent compound to a biological compartment (e.g., the brain or lymphatic system) relative to the parent species.

Examples of pharmaceutically acceptable prodrugs of the compounds of this invention include, without limitation, esters, amino acid esters, phosphate esters, metal salts and sulfonate esters.

The compounds of this invention can exist in free form for treatment, or where appropriate, as a pharmaceutically acceptable salt.

As used herein, the term "pharmaceutically acceptable salt" refers to salts of a compound which are, within the scope of sound medical judgment, suitable for use in contact with the tissues of humans and lower animals without undue toxicity, irritation, allergic response and the like, and are commensurate with a reasonable benefit/risk ratio.

Pharmaceutically acceptable salts of the compounds of this invention include those derived from suitable inorganic and organic acids and bases. These salts can be prepared in situ during the final isolation and purification of the compounds. Acid addition salts can be prepared by 1) reacting the purified compound in its free-based form with a suitable organic or inorganic acid and 2) isolating the salt thus formed.

Examples of suitable acid salts include acetate, adipate, alginate, aspartate, benzoate, benzenesulfonate, bisulfate, butyrate, citrate, camphorate, camphorsulfonate, cyclopentanepropionate, digluconate, dodecylsulfate, ethanesulfonate, formate, fumarate, glucoheptanoate, glycerophosphate, glycolate, hemisulfate, heptanoate, hexanoate, hydrochloride, hydrobromide, hydroiodide, 2-hydroxyethanesulfonate, lactate, maleate, malonate, methanesulfonate, 2-naphthalenesulfonate, nicotinate, nitrate, oxalate, palmoate, pectinate, persulfate, 3-phenylpropionate, phosphate, picrate, pivalate, propionate, salicylate, succinate, sulfate, tartrate, thiocyanate, tosylate and undecanoate. Other acids, such as oxalic, while not in themselves pharmaceutically acceptable, may be employed in the preparation of salts useful as intermediates in obtaining the compounds of the invention and their pharmaceutically acceptable acid addition salts.

Base addition salts can be prepared by 1) reacting the purified compound in its acid form with a suitable organic or inorganic base and 2) isolating the salt thus formed.

Salts derived from appropriate bases include alkali metal (e.g., sodium and potassium), alkaline earth metal (e.g., magnesium), ammonium and $N^+(C_{1-4}$ alkyl$)_4$ salts. This invention also envisions the quaternization of any basic nitrogen-containing groups of the compounds disclosed herein. Water or oil-soluble or dispersible products may be obtained by such quaternization.

Base addition salts also include alkali or alkaline earth metal salts. Representative alkali or alkaline earth metal salts include sodium, lithium, potassium, calcium, magnesium, and the like. Further pharmaceutically acceptable salts include, when appropriate, nontoxic ammonium, quaternary ammonium, and amine cations formed using counterions such as halide, hydroxide, carboxylate, sulfate, phosphate, nitrate, loweralkyl sulfonate and aryl sulfonate. Other acids and bases, while not in themselves pharmaceutically acceptable, may be employed in the preparation of salts useful as intermediates in obtaining the compounds of the invention and their pharmaceutically acceptable acid or base addition salts.

Pharmaceutically acceptable carriers that may be used in these pharmaceutical compositions include, but are not limited to, ion exchangers, alumina, aluminum stearate, lecithin, serum proteins, such as human serum albumin, buffer substances such as phosphates, glycine, sorbic acid, potassium sorbate, partial glyceride mixtures of saturated vegetable fatty acids, water, salts or electrolytes, such as protamine sulfate, disodium hydrogen phosphate, potassium hydrogen phosphate, sodium chloride, zinc salts, colloidal silica, magnesium trisilicate, polyvinyl pyrrolidone, cellulose-based substances, polyethylene glycol, sodium carboxymethylcellulose, polyacrylates, waxes, polyethylene-polyoxypropylene-block polymers, polyethylene glycol and wool fat.

The compositions of the present invention may be administered orally, parenterally, by inhalation spray, topically, rectally, nasally, buccally, vaginally or via an implanted reservoir. The term "parenteral" as used herein includes subcutaneous, intravenous, intramuscular, intra-articular, intra-synovial, intrasternal, intrathecal, intraperitoneal, intrahepatic, intralesional and intracranial injection or infusion techniques.

Sterile injectable forms of the compositions of this invention may be aqueous or oleaginous suspension. These suspensions may be formulated according to techniques known in the art using suitable dispersing or wetting agents and suspending agents. The sterile injectable preparation may also be a sterile injectable solution or suspension in a non-toxic parenterally-acceptable diluent or solvent, for example as a solution in 1,3-butanediol. Among the acceptable vehicles and solvents that may be employed are water, Ringer's solution and isotonic sodium chloride solution. In addition, sterile, fixed oils are conventionally employed as a solvent or suspending medium. For this purpose, a bland fixed oil may be employed including synthetic mono- or di-glycerides. Fatty acids, such as oleic acid and its glyceride derivatives are useful in the preparation of injectables, as are natural pharmaceutically-acceptable oils, such as olive oil or castor oil, especially in their polyoxyethylated versions. These oil solutions or suspensions may also contain a long-chain alcohol diluent or dispersant, such as carboxymethyl cellulose or similar dispersing agents which are commonly used in the formulation of pharmaceutically acceptable dosage forms including emulsions and suspensions. Other commonly used surfactants, such as Tweens, Spans and other emulsifying agents or bioavailability enhancers which are commonly used in the manufacture of pharmaceutically acceptable solid, liquid, or other dosage forms may also be used for the purposes of formulation.

The pharmaceutical compositions of this invention may be orally administered in any orally acceptable dosage form including, but not limited to, capsules, tablets, aqueous suspensions or solutions. In the case of tablets for oral use, carriers commonly used may include lactose and corn starch. Lubricating agents, such as magnesium stearate, may also be added. For oral administration in a capsule form, useful diluents may include lactose and dried cornstarch. When aqueous suspensions are required for oral use, the active ingredient may be combined with emulsifying and suspending agents. If desired, certain sweetening, flavoring or coloring agents may also be added.

Alternatively, the pharmaceutical compositions of this invention may be administered in the form of suppositories for rectal administration. These can be prepared by mixing the agent with a suitable non-irritating excipient which is solid at room temperature but liquid at rectal temperature and therefore will melt in the rectum to release the drug. Such materials may include cocoa butter, beeswax and polyethylene glycols.

The pharmaceutical compositions of this invention may also be administered topically, especially when the target of treatment includes areas or organs readily accessible by topical application, including diseases of the eye, the skin, or the lower intestinal tract. Suitable topical formulations may be prepared for each of these areas or organs.

Topical application for the lower intestinal tract can be effected in a rectal suppository formulation (see above) or in a suitable enema formulation. Topically-transdermal patches may also be used.

For topical applications, the pharmaceutical compositions may be formulated in a suitable ointment containing the active component suspended or dissolved in one or more carriers. Carriers for topical administration of the compounds of this invention may include, but are not limited to, mineral oil, liquid petrolatum, white petrolatum, propylene glycol, polyoxyethylene, polyoxypropylene compound, emulsifying wax and water. Alternatively, the pharmaceutical compositions may be formulated in a suitable lotion or cream containing the active components suspended or dissolved in one or more pharmaceutically acceptable carriers. Suitable carriers may include, but are not limited to, mineral oil, sorbitan monostearate, polysorbate 60, cetyl esters wax, cetearyl alcohol, 2-octyldodecanol, benzyl alcohol and water.

For ophthalmic use, the pharmaceutical compositions may be formulated as micronized suspensions in isotonic, pH adjusted sterile saline, or as solutions in isotonic, pH adjusted sterile saline, either with or without a preservative such as benzylalkonium chloride. Alternatively, for ophthalmic uses, the pharmaceutical compositions may be formulated in an ointment such as petrolatum.

The pharmaceutical compositions of this invention may also be administered by nasal aerosol or inhalation. Such compositions may be prepared as solutions in saline, employing benzyl alcohol or other suitable preservatives, absorption promoters to enhance bioavailability, fluorocarbons, and/or other conventional solubilizing or dispersing agents.

The amount of kinase inhibitor that may be combined with the carrier materials to produce a single dosage form will vary depending upon the host treated, the particular mode of administration, and the indication. In an embodiment, the compositions should be formulated so that a dosage of between 0.01-100 mg/kg body weight/day of the inhibitor can be administered to a patient receiving these compositions. In another embodiment, the compositions should be formulated so that a dosage of between 0.1-100 mg/kg body weight/day of the inhibitor can be administered to a patient receiving these compositions.

It should also be understood that a specific dosage and treatment regimen for any particular patient will depend upon a variety of factors, including the activity of the specific compound employed, the age, body weight, general health, sex, diet, time of administration, rate of excretion, drug combination, and the judgment of the treating physician and the severity of the particular disease being treated. The amount of inhibitor will also depend upon the particular compound in the composition.

According to another embodiment, the invention provides methods for treating or preventing cancer, a proliferative disorder, or a myeloproliferative disorder comprising the step of administering to a patient one of the herein-described compounds or pharmaceutical compositions.

The term "patient", as used herein, means an animal, including a human.

In some embodiments, said method is used to treat or prevent a hematopoietic disorder, such as acute-myelogenous leukemia (AML), acute-promyelocytic leukemia (APL), chronic-myelogenous leukemia (CML), or acute lymphocytic leukemia (ALL).

In other embodiments, said method is used to treat or prevent myeloproliferative disorders, such as polycythemia vera, thrombocythemia, myeloid metaplasia with myelofibrosis, chronic myelogenous leukaemia (CML), chronic myelomonocytic leukemia, hypereosinophilic syndrome, juvenile myelomonocytic leukemia, and systemic mast cell disease.

In yet other embodiments, said method is used to treat or prevent cancer, such as cancers of the breast, colon, prostate, skin, pancreas, brain, genitourinary tract, lymphatic system, stomach, larynx and lung, including lung adenocarcinoma, small cell lung cancer, and non-small cell lung cancer.

Another embodiment provides a method of treating or preventing cancer comprising the step of administering to a patient a compound of formula I or a composition comprising said compound.

Another aspect of the invention relates to inhibiting kinase activity in a patient, which method comprises administering to the patient a compound of formula I or a composition comprising said compound. In some embodiments, said kinase is an Aurora kinase (Aurora A, Aurora B, Aurora C), Abl, Abl(T315I), Arg, FLT-3, JAK-2, MLK1, PLK4, Tie2, or TrkA.

Depending upon the particular conditions to be treated or prevented, additional drugs may be administered together with the compounds of this invention. In some cases, these additional drugs are normally administered to treat or prevent the same condition. For example, chemotherapeutic agents or other anti-proliferative agents may be combined with the compounds of this invention to treat proliferative diseases.

Another aspect of this invention is directed towards a method of treating cancer in a subject in need thereof, comprising the sequential or co-administration of a compound of this invention or a pharmaceutically acceptable salt thereof, and another therapeutic agent. In some embodiments, said additional therapeutic agent is selected from an anti-cancer agent, an anti-proliferative agent, or a chemotherapeutic agent.

In some embodiments, said additional therapeutic agent is selected from camptothecin, the MEK inhibitor: U0126, a KSP (kinesin spindle protein) inhibitor, adriamycin, interferons, and platinum derivatives, such as Cisplatin.

In other embodiments, said additional therapeutic agent is selected from taxanes; inhibitors of bcr-abl (such as Gleevec, dasatinib, and nilotinib); inhibitors of EGFR (such as Tarceva and Iressa); DNA damaging agents (such as cisplatin, oxaliplatin, carboplatin, topoisomerase inhibitors, and anthracyclines); and antimetabolites (such as AraC and 5-FU).

In yet other embodiments, said additional therapeutic agent is selected from camptothecin, doxorubicin, idarubicin, Cisplatin, taxol, taxotere, vincristine, tarceva, the MEK inhibitor, U0126, a KSP inhibitor, vorinostat, Gleevec, dasatinib, and nilotinib.

In another embodiment, said additional therapeutic agent is selected from Her-2 inhibitors (such as Herceptin); HDAC inhibitors (such as vorinostat), VEGFR inhibitors (such as Avastin), c-KIT and FLT-3 inhibitors (such as sunitinib), BRAF inhibitors (such as Bayer's BAY 43-9006) MEK inhibitors (such as Pfizer's PD0325901); and spindle poisons (such as Epothilones and paclitaxel protein-bound particles (such as Abraxane®)

Other therapies or anticancer agents that may be used in combination with the inventive anticancer agents of the present invention include surgery, radiotherapy (in but a few examples, gamma-radiation, neutron beam radiotherapy, electron beam radiotherapy, proton therapy, brachytherapy, and systemic radioactive isotopes, to name a few), endocrine therapy, biologic response modifiers (interferons, interleukins, and tumor necrosis factor (TNF) to name a few), hyperthermia and cryotherapy, agents to attenuate any adverse effects (e.g., antiemetics), and other approved chemotherapeutic drugs, including, but not limited to, alkylating drugs (mechlorethamine, chlorambucil, Cyclophosphamide, Melphalan, Ifosfamide), antimetabolites (Methotrexate), purine antagonists and pyrimidine antagonists (6-Mercaptopurine, 5-Fluorouracil, Cytarabile, Gemcitabine), spindle poisons (Vinblastine, Vincristine, Vinorelbine, Paclitaxel), podophyllotoxins (Etoposide, Irinotecan, Topotecan), antibiotics (Doxorubicin, Bleomycin, Mitomycin), nitrosoureas (Carmustine, Lomustine), inorganic ions (Cisplatin, Carboplatin), enzymes (Asparaginase), and hormones (Tamoxifen, Leuprolide, Flutamide, and Megestrol), Gleevec™, dexamethasone, and cyclophosphamide.

A compound of the instant invention may also be useful for treating cancer in combination with the following therapeutic agents: abarelix (Plenaxis depot®); aldesleukin (Prokine®); Aldesleukin (Proleukin®); Alemtuzumabb (Campath®); alitretinoin (Panretin®); allopurinol (Zyloprim®); altretamine (Hexylen®); amifostine (Ethyol®); anastrozole (Arimidex®); arsenic trioxide (Trisenox®); asparaginase (Elspar®); azacitidine (Vidaza®); bevacuzimab (Avastin®); bexarotene capsules (Targretin®); bexarotene gel (Targretin®); bleomycin (Blenoxane®); bortezomib (Velcade®); busulfan intravenous (Busulfex®); busulfan oral (Myleran®); calusterone (Methosarb®); capecitabine (Xeloda®); carboplatin (Paraplatin®); carmustine (BCNU®, BiCNU®); carmustine (Gliadel®); carmustine with Polifeprosan 20 Implant (Gliadel Wafer®); celecoxib (Celebrex®); cetuximab (Erbitux®); chlorambucil (Leukeran®); cisplatin (Platinol®); cladribine (Leustatin®, 2-CdA®); clofarabine (Clolar®); cyclophosphamide (Cytoxan®, Neosar®); cyclophosphamide (Cytoxan Injection®); cyclophosphamide (Cytoxan Tablet®); cytarabine (Cytosar-U®); cytarabine liposomal (DepoCyt®); dacarbazine (DTIC-Dome®); dactinomycin, actinomycin D (Cosmegen®); Darbepoetin alfa (Aranesp®); daunorubicin liposomal (DanuoXome®); daunorubicin, daunomycin (Daunorubicin®); daunorubicin, daunomycin (Cerubidine®); Denileukin diftitox (Ontak®); dexrazoxane (Zinecard®); docetaxel (Taxotere®); doxorubicin (Adriamycin PFS®); doxorubicin (Adriamycin®, Rubex®); doxorubicin (Adriamycin PFS Injection®); doxorubicin liposomal (Doxil®); dromostanolone propionate (dromostanolone®); dromostanolone propionate (masterone injection®); Elliott's B Solution (Elliott's B Solution®); epirubicin (Ellence®); Epoetin alfa (epogen®); erlotinib (Tarceva®); estramustine (Emcyt®); etoposide phosphate (Etopophos®); etoposide, VP-16 (Vepesid®); exemestane (Aromasin®); Filgrastim (Neupogen®); floxuridine (intraarterial) (FUDR®); fludarabine (Fludara®); fluorouracil, 5-FU (Adrucil®); fulvestrant (Faslodex®); gefitinib (Iressa®); gemcitabine (Gemzar®); gemtuzumab ozogamicin (Mylotarg®); goserelin acetate (Zoladex Implant®); goserelin acetate (Zoladex®); histrelin acetate (Histrelin implant®); hydroxyurea (Hydrea®); Ibritumomab Tiuxetan (Zevalin®); idarubicin (Idamycin®); ifosfamide (IFEX®); imatinib mesylate (Gleevec®); interferon alfa 2a (Roferon A®); Interferon alfa-2b (Intron A®); irinotecan (Camptosar®); lenalidomide (Revlimid®); letrozole (Femara®); leucovorin (Wellcovorin®, Leucovorin®); Leuprolide Acetate (Eligard®); levamisole (Ergamisol®); lomustine, CCNU (CeeBU®); meclorethamine, nitrogen mustard (Mustargen®); megestrol acetate (Megace®); melphalan, L-PAM (Alkeran®); mercaptopurine, 6-MP (Purinethol®); mesna (Mesnex®); mesna (Mesnex tabs®); methotrexate (Methotrexate®); methoxsalen (Uvadex®); mitomycin C (Mutamycin®); mitotane (Lysodren®); mitoxantrone (Novantrone®); nandrolone phenpropionate (Durabolin-50®); nelarabine (Arranon®); Nofetumomab (Verluma®); Oprelvekin (Neumega®); oxaliplatin (Eloxatin®); paclitaxel (Paxene®); paclitaxel (Taxol®); paclitaxel protein-bound particles (Abraxane®); palifermin (Kepivance®); pamidronate (Aredia®); pegademase (Adagen (Pegademase Bovine)®); pegaspargase (Oncaspar®); Pegfilgrastim (Neulasta®); pemetrexed disodium (Alimta®); pentostatin (Nipent®); pipobroman (Vercyte®); plicamycin, mithramycin (Mithracin®); porfimer sodium (Photofrin®); procarbazine (Matulane®); quinacrine (Atabrine®); Rasburicase (Elitek®); Rituximab (Rituxan®); sargramostim (Leukine®); Sargramostim (Prokine®); sorafenib (Nexavar®); streptozocin (Zanosar®); sunitinib maleate (Sutent®); talc (Sclerosol®); tamoxifen (Nolvadex®); temozolomide (Temodar®); teniposide, VM-26 (Vumon®); testolactone (Teslac®); thioguanine, 6-TG (Thioguanine®); thiotepa (Thioplex®); topotecan (Hycamtin®); toremifene (Fareston®); Tositumomab (Bexxar®); Tositumomab/1-131 tositumomab (Bexxar®); Trastuzumab (Herceptin®); tretinoin, ATRA (Vesanoid®); Uracil Mustard (Uracil Mustard Capsules®); valrubicin (Valstar®); vinblastine (Velban®); vincristine (Oncovin®); vinorelbine (Navelbine®); zoledronate (Zometa®) and vorinostat (Zolinza®).

For a comprehensive discussion of updated cancer therapies see, http://www.nci.nih.gov/, a list of the FDA approved oncology drugs at http://www.fda.gov/cder/cancer/druglistframe.htm, and The Merck Manual, Seventeenth Ed. 1999, the entire contents of which are hereby incorporated by reference.

Another embodiment provides a simultaneous, separate or sequential use of a combined preparation.

Those additional agents may be administered separately, as part of a multiple dosage regimen, from the kinase inhibitor-containing compound or composition. Alternatively, those agents may be part of a single dosage form, mixed together with the kinase inhibitor in a single composition.

In order that this invention be more fully understood, the following preparative and testing examples are set forth. These examples are for the purpose of illustration only and are not to be construed as limiting the scope of the invention in any way. All documents cited herein are hereby incorporated by reference.

EXAMPLES

As used herein, the term "Rt(min)" refers to the HPLC retention time, in minutes, associated with the compound. Unless otherwise indicated, the HPLC method utilized to obtain the reported retention time is as follows:

Column: ACE C8 column, 4.6×150 mm
Gradient: 0-100% acetonitrile+methanol 60:40 (20 mM Tris phosphate)
Flow rate: 1.5 mL/minute
Detection: 225 nm.

Mass spec. samples were analyzed on a MicroMass Quattro Micro mass spectrometer operated in single MS mode with electrospray ionization. Samples were introduced into the mass spectrometer using chromatography. Mobile phase for all mass spec. analyses consisted of 10 mM pH 7 ammonium acetate and a 1:1 acetonitrile-methanol mixture, column gradient conditions was 5%-100% acetonitrile-methanol over 3.5 mins gradient time and 5 mins run time on an ACE C8 3.0×75 mm column. Flow rate was 1.2 ml/min.

$^1$H-NMR spectra were recorded at 400 MHz using a Bruker DPX 400 instrument. The following compounds of formula I were prepared and analyzed as follows.

Example 1

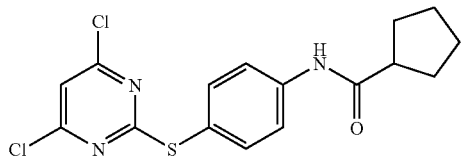

N-(4-(4,6-dichloropyrimidin-2-ylthio)phenyl)cyclopentane carboxamide

A solution of 4,6-dichloro-2-(methylsulfonyl)pyrimidine (1.96 g, 8.69 mmol) and N-(4-mercaptophenyl)cyclopentanecarboxamide (2.06 g, 8.69 mmol) in acetonitrile (40 ml) was cooled to 0° C. Triethylamine (0.88 g, 8.69 mmol, 1.21 ml) was added dropwise and the solution stirred for 10 mins at 0° C. for 10 mins and then at room temperature for 2 hrs. Water (15 ml) was added and the suspension filtered, washing with water (30 ml), and then dried to give the title compound as a pale yellow solid (1.87 g, 49%). 1H NMR (DMSO-d6) 1.50-1.61 (2H, m), 1.65-1.78 (4H, m), 1.82-1.93 (2H, m), 2.76-1.82 (1H, m), 7.52 (2H, d), 1.70-1.75 (3H, m), 10.08 (1H, s). ES+ 368.

Example 2

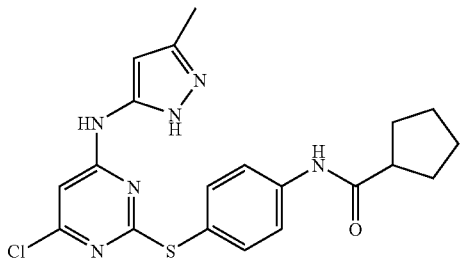

N-(4-(4-(3-methyl-1H-pyrazol-5-ylamino)-6-chloro-pyrimidin-2-ylthio)phenyl)cyclopentanecarboxamide To a solution of 3-methyl-1H-pyrazol-5-amine (160 mg, 1.63 mmol) and N-(4-(4,6-dichloropyrimidin-2-ylthio)phenyl)cyclopentane carboxamide (600 mg, 1.63 mmol) in dimethyl formamide (10 ml) was added diisopropylethylamine (248 mg, 1.96 mmol, 0.34 ml). The mixture was then heated to 80 ° C. for 18 hrs and allowed to cool to rt. EtOAc (40 ml) was added and washed with brine, dried (MgSO4), and concentrated in vacuo. Crude product was then purified by flash chromatography 7:3 EtOAc:hexane ÆEtOAc Æ5% MeOH:EtOAc to give title compound as an off white solid (431 mg, 62%). 1H NMR (DMSO-d6) 1.50-1.55 (2H, m), 1.61-1.78 (4H, m), 1.79-1.85 (2H, m), 1.90 (3H, brs), 2.72-1.81 (1H, m), 5.21 (1H, brs), 6.46 (1H, brs), 7.52 (2H, d), 7.78 (2H, d), 10.11 (1H, s), 10.18 (1H, brs), 11.95 (1H, brs). ES+ 429.

Example 3

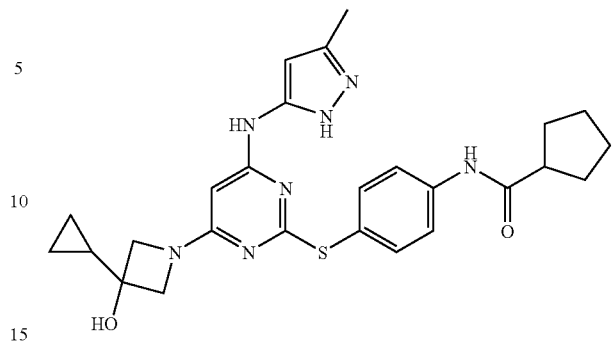

N-(4-((4-(3-methyl-1H-pyrazol-5-ylamino)-6-(3-cyclopropyl-3-hydroxyazetidin-1-yl)pyrimidin-2-yl)sulfanyl)phenyl)cyclopentanecarboxamide (I-9)

To a suspension of N-(4-(4-(3-methyl-1H-pyrazol-5-ylamino)-6-chloropyrimidin-2-ylthio)phenyl)cyclopentanecarboxamide (200 mg, 0.47 mmol) and 3-cyclopropyl azetidin-3-ol hydrochloride (70 mg, 0.47 mmol) in n-BuOH (5 ml) was added diisopropylethylamine (239 mg, 1.88 mmol, 0.30 ml). The mixture was heated to 100° C. for 16 hrs and then allowed to cool to room temperature and diluted with EtOAc (30 ml) and sat NaHCO-3. The organic layer washed with brine, dried (Na2SO4) and concentrated. Crude product was then purified by flash chromatography EtOAc Æ5% MeOH:EtOAc to give title compound as an off white solid (70 mg, 30%). 1H NMR (DMSO-d6) 0.30-0.35 (2H, m), 0.39-0.44 (2H, m), 1.16-1.21 (1H, m), 1.56-1.75 (6H, m), 1.83-1.90 (2H, m), 2.00 (3H, s), 2.76-2.82 (1H, m), 3.65 (4H, dd), 5.35 (1H, s), 5.58 (1H, s), 7.47 (2H, d), 7.72 (2H, d), 9.19 (1H, s), 10.06 (1H, s), 11.65 (1H, s). ES+ 506.

Table 2 below depicts data for certain exemplary compounds made according to the method described in Scheme I and in Examples 1-3. Compound numbers correspond to those compounds depicted in Table 1.

TABLE 2

| Compound No | M + 1 (obs) | 1H NMR | Rt(mins) |
|---|---|---|---|
| I-1 | 496.00 | (DMSO-d6): 0.98(9H, s), 1.10(3H, t), 1.66(2H, brs), 1.98(3H, brs), 2.34(2H, q), 3.69(2H, d), 3.83(2H, d), 5.35(1H, brs), 5.70(1H, s), 5.75(1H, vbrs), 7.46(2H, d), 7.70(2H, d), 9.18(1H, brs), 10.08(1H, s), 11.68(1H, brs). | 8.93 |
| I-2 | 466.00 | (DMSO-d6): 0.29-0.33(2H, m), 0.40-0.49(2H, m), 1.10(3H, t), 1.18-1.21(1H, m), 1.99(3H, brs), 2.34(2H, q), 3.63(2H, d), 3.68(2H, d), 5.36(1H, s), 5.60(1H, s), 7.47(2H, d), 7.70(2H, d), 9.21(1H, brs), 10.08(1H, s), 11.67(1H, brs). | 7.63 |
| I-3 | 494.50 | (DMSO-d6): 1.15(3H, t), 1.3-1.4(2H, m), 1.5-1.8(6H, m), 2.02(3H, s), 2.17-2.23(1H, m), 2.42(2H, q), 3.68(2H, d), 3.82(2H, d), 5.5(1H, s), 5.65(1H, s), 5.72(1H, brs), 7.52(2H, d), 7.78(2H, d), 9.22(1H, brs), 10.12(1H, s), 11.7(1H, brs) | 8.9 |
| I-4 | 454.00 | (DMSO-d6): 0.89(3H, t), 1.10(3H, t), 1.65(2H, brq), 1.99(3H, brs), 2.35(2H, q), 3.64(2H, d), 3.75(2H, d), 5.38(1H, brs), 5.51(1H, s), 5.62(1H, vbrs), 7.47(2H, d), 7.70(2H, d), 9.16(1H, brs), 10.05(1H, s), 11.65(1H, brs). | 7.87 |
| I-5 | 468.00 | (DMSO-d6): 0.87(6H, d), 1.10(3H, t), 1.81(1H, sep), 1.99(3H, brs), 2.34(2H, q), 3.61(2h, d), 3.81(2H, d), 5.37(1H, brs), 5.47(1H, brs), 5.63(1H, vbrs), 7.47(2H, d), 7.70(2H, d), 9.17(1H, brs), 10.05(1H, s), 11.65(1H, brs). | 8.35 |

TABLE 2-continued

| Compound No | M + 1 (obs) | 1H NMR | Rt(mins) |
|---|---|---|---|
| I-6 | 482.49 | (DMSO-d6): 0.90-0.83(6H, m), 1.12-1.08(4H, m), 1.54-1.46(2H, m), 2.02(3H, s), 2.35(2H, q), 3.14(1H, br m), 3.68(2H, t), 3.88(2H, t), 5.40(1H, s), 5.61(1H, br s), 7.50(2H, d), 7.72(2H, d), 9.63(1H, br s), 10.14(1H, s). | 8.830 |
| I-7 | 492.84 | (DMSO-d6): 0.32(2H, d), 0.41(2H, d), 0.53(2H, d), 0.82(2H, d), 1.08(3H, t), 1.20(1H, m), 1.70(1H, m), 2.34(2H, q), 3.65(4H, q), 5.34(1H, s), 5.68(1H, br s), 7.52(2H, d), 7.71(2H, d), 9.33(1H, s), 10.04(1H, s) | 8.402 |
| I-8 | 478.78 | (DMSO-d6): 0.34(2H, d), 0.40(2H, d), 0.81(4H, d), 1.19(1H, m), 1.81(1H, m), 2.01(3H, s), 3.66(4H, q), 5.40(1H, s), 5.61(1H, br s), 7.48(2H, d), 7.71(2H, d), 9.37(1H, s), 10.39(1H, s) | 8.229 |
| I-9 | 506.00 | (DMSO-d6): 0.30-0.35(2H, m), 0.39-0.44(2H, m), 1.16-1.21(1H, m), 1.56-1.75(6H, m), 1.83-1.90(2H, m), 2.00(3H, s), 2.76-2.82(1H, m), 3.65(4H, dd), 5.35(1H, s), 5.58(1H, s), 7.47(2H, d), 7.72(2H, d), 9.19(1H, s), 10.06(1H, s), 11.65(1H, s). | 8.938 |
| I-10 | 504.83 | (DMSO-d6): 0.32(2H, d), 0.42(2H, d), 0.55(2H, m), 0.82(6H, m), 1.19(1H, m), 1.70(1H, m), 1.80(1H, m), 3.65(4H, q), 5.43(1H, s), 5.65(1H, br s), 7.47(2H, d), 7.69(2H, d), 9.68(1H, s), 10.42(1H, s) | 8.544 |
| I-12 | 514.80 | (DMSO-d6): 0.35-0.41(2H, m), 0.45-0.51(2H, m), 1.2-1.28(2H, m), 2.1-2.15(5H, m), 2.8-2.9(1H, m), 3.68-3.75(4H, m), 5.45(1H, s), 5.65(1H, brs), 7.58(2H, d), 7.78(2H, d), 9.23(1H, brs), 10.7(1H, s), 11.7(1H, brs) | 8.18 |
| I-13 | 480.00 | (MeOD): 0.40-0.45(2H, m), 0.57-0.62(2H, m), 0.80-0.85(2H, m), 0.90-0.95(2H, m), 1.30-1.40(1H, m), 1.80-1.85(1H, m), 2.05-2.10(1H, s), 3.80-4.00(4H, m), 5.40-5.50(2H, m), 7.50-7.55(2H, d), 7.65-7.70(2H, d). | 9.148 |
| I-14 | 522.00 | (MeOD): 0.40-0.45(2H, m), 0.60-0.65(2H, m), 1.3-1.4(1H, m), 2.05(2H, s), 3.25-3.40(2H, m), 3.85-3.40(4H, m), 5.40-5.50(2H, m), 7.50-7.55(2H, d), 7.65-7.70(2H, d). | 9.235 |
| I-15 | 548.00 | (MeOD): 0.35-0.40(2H, m), 0.55-0.60(2H, m), 1.25-1.35(6H, m), 2.0(3H, m), 3.80-3.90(4H, m), 5.35-5.40(2H, m), 7.45-7.50(2H, d), 7.60-7.65(2H, d). | 9.715 |
| I-16 | 468.40 | CD$_3$OD: 0.80(2H, m), 1.10(2H, d), 1.65(3H, t), 1.90(1H, m), 2.50(3H, s), 2.88(2H, q), 4.40(4H, m), 5.94(2H, m), 7.49(2H, d), 8.10(2H, d). | 9.035 |
| I-17 | 536.36 | (DMSO-d6): 0.42-0.46(2H, m), 0.60-0.63(2H, m), 1.4(1H, m), 1.98(3H, s), 2.59-2.68(4H, m), 3.80-3.93(4H, m), 5.36(1H, brs), 5.75(1H, brs), 7.50-7.52(2H, d), 7.69-7.71(2H, d), 9.37(1H, s), 10.31(1H, s) and 11.75(1H, brs); | 9.58 |

Example 4

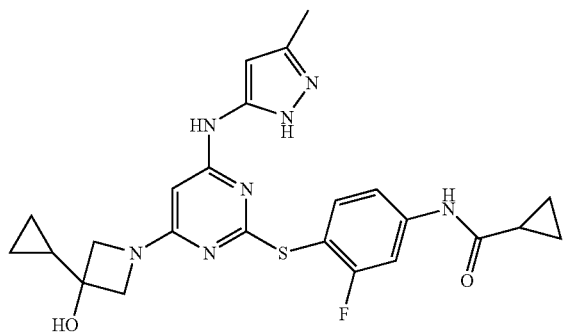

N-(4-((4-(3-methyl-1H-pyrazol-5-ylamino)-6-(3-cyclopropyl-3-hydroxyazetidin-1-yl)pyrimidin-2-yl)sulfanyl)-3-fluorophenyl)cyclopropanecarboxamide (I-11)

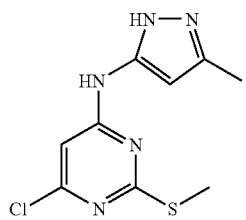

6-Chloro-N-(3-methyl-1H-pyrazol-5-yl)-2-(methylthio)pyrimidin-4-amine

To a stirred solution of 4,6-dichloro-2-(methylthio)pyrimidine (25 g, 0.128 mol) in DMF (100 ml) was added diisopropylamine (19.8 g, 0.154 mol) followed by 3-amino-5-methylpyrazole (13.7 g, 0.154 mol) portionwise over 10 minutes. The solution was heated to 50° C. for 16 hours, after which time all of the starting material had reacted (by LC/MS analysis). The mixture was cooled to ambient and poured into water (250 ml). The precipitate was filtered and the wet solid slurried in diethyl ether (300 ml). The solid was again filtered and re-slurried in methanol (100 ml). The filtered product was air dried on the sinter, then further dried under vacuum. This afford the title compound as an off-white solid (22.1 g, 66% yield). $^1$H NMR (d6-DMSO) δ 2.22 (3H, s, CH$_3$), 3.31 (3H, s, CH$_3$), 6.00-7.50 (2H, br, CH), 10.17 (1H, s, NH), 12.10 (1H, s, NH); MS ES+256.08, ES−254.25.

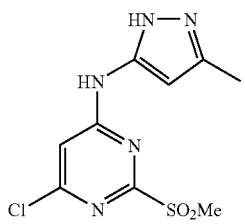

6-chloro-N-(3-methyl-1H-pyrazol-5-yl)-2-(methylsulfonyl)pyrimidin-4-amine

To a stirred suspension of 6-chloro-N-(3-methyl-1H-pyrazol-5-yl)-2-(methylsulfinyl)pyrimidin-4-amine (8 g, 31.2 mmol) in methanol (200 ml) at 0° C. was added a suspension of Oxone (44 g, 71.7 mmol) in water (100 ml) portionwise over 10 minutes. The mixture was stirred for 30 minutes at 0° C. then warmed to ambient and stirred for an additional 2 hours. The reaction mixture was filtered and the resulting solid slurried in aqueous sodium bicarbonate. The mixture was filtered and the solid washed with water, then diethyl ether. The solid was slurried in ethyl acetate, filtered and dried. This gave the title product as an off-white solid (7.9 g, 88%); $^1$H NMR (d6-DMSO) δ 2.24 (3H, s), 3.35 (3H, s), 5.85 (0.5H, brs), 6.50 (0.5H, brs), 6.95 (0.5H, brs), 8.00 (0.5H, brs), 10.95 (1H, s), 12.28 (1H, s); MS ES+288.07, ES−286.25.

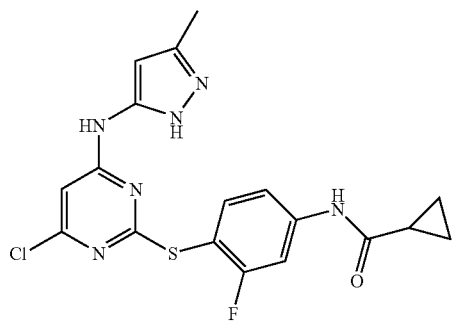

N-(4-(4-(3-methyl-1H-pyrazol-5-ylamino)-6-chloropyrimidin-2-ylthio)-3-fluorophenyl)cyclopropanecarboxamide A solution of N-(3-fluoro-4-mercaptophenyl)cyclopropane-carboxamide (1.0 g, 4.8 mmol) and 6-chloro-N-(3-methyl-1H-pyrazol-5-yl)-2-(methylsulfonyl)pyrimidin-4-amine (1.4 g, 4.8 mmol) in t-butanol (10 ml) was heated 70° C. for 18 h. Reaction mixture cooled to room temperature then diluted with EtOAc (60 ml), washed with sat. NaHCO3 solution (30 ml), brine (30 ml), dried (MgSO4), filtered and concentrated in vacuo. Crude product was purified by flash chromatography on silica (EtOAc/Petrol 20 to 60%) to give the title compound as white solid (800 mg, 40%). ES+ 419.

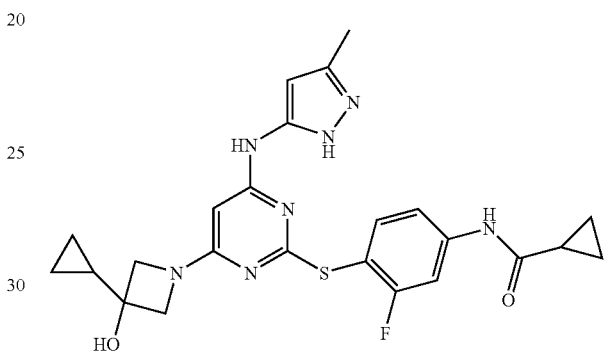

N-(4-((4-(3-methyl-1H-pyrazol-5-ylamino)-6-(3-cyclopropyl-3-hydroxyazetidin-1-yl)pyrimidin-2-yl)sulfanyl)-3-fluorophenyl)cyclopropanecarboxamide (I-11)

A mixture of N-(4-(4-(3-methyl-1H-pyrazol-5-ylamino)-6-chloropyrimidin-2-ylthio)-3-fluorophenyl)cyclopropane-carboxamide (160 mg, 0.38 mmol), 3-cyclopropylazetidin-3-ol hydrochloride (70 mg, 0.49 mmol) and DIPEA (0.20 ml) in n-butanol (1.5 ml) were heated in microwave at 130 ° C. for 1 h. Reaction mixture was then cooled to room temperature, diluted with EtOAc (20 ml), washed with sat NaHCO3 solution (10 ml), water (2×10 ml), brine (10 ml), dried (MgSO4), filtered and evaporated in vacuo. Crude product was purified by flash chromatography on silica (EtOAc/Petrol 30 to 80%) to give the title compound as a white solid (55 mg, 29%). 1H NMR (DMSO-d6) 0.33-0.36 (2H, m), 0.42-0.48 (2H, m), 0.82-0.86 (4H, m), 1.21-1.24 (2H, m), 1.85-1.89 (1H, m), 2.08 (3H, s), 2.10-2.15 (1H, m), 3.66-3.75 (4H, m), 5.42 (1H, br s), 5.67 (1H, 1H, s), 5.8 (1H, br s), 7.42 (1H, d), 7.52-7.58 (1H, m), 7.75 (1H, d), 9.27 (1H, s), 10.65 (1H, s), 11.9 (1H, br s). ES+ 496.90.

Table 3 below depicts data for certain exemplary compounds made according to the method described in the General Scheme (Method B) and in Example 6. Compound numbers correspond to those compounds depicted in Table 1.

TABLE 3

| Compound No | M + 1 (obs) | 1H NMR | Rt(mins) |
|---|---|---|---|
| I-11 | 496.90 | (DMSO-d6): 0.33-0.36(2H, m), 0.42-0.48(2H, m), 0.82-0.86(4H, m), 1.21-1.24(2H, m), 1.85-1.89(1H, m), 2.08(3H, s), 2.10-2.15(1H, m), 3.66-3.75(4H, m), 5.42(1H, brs), 5.67(1H, s), 5.8(1H, brs), 7.42(1H, d), 7.52-7.58(1H, m), 7.75(1H, d), 9.27(1H, s), 10.65(1H, s), 11.9(1H, brs) | 8.52 |
| I-19 | 494.58 | (DMSO-d6): 0.20(2H, m), 0.42-0.51(4H, m), 0.59(2H,), 1.07(1H, m), 1.40(1H, m), 1.99(3H, m), 2.24(2H, m), 3.81-3.94(4H, m), 5.36(1H, s), 5.70(1H, br s), 7.47(2H, m), 7.72(2H, m), 9.27(1H, s), 9.99(1H, s), 11.65(1H, br s) | 9.304 |

Example 5

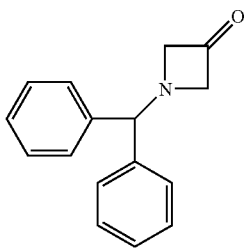

N-Benzhydrylazetidin-3-one

To a stirred slurry of 1-(diphenylmethyl)-3-hydroxyazetidine (30 g, 0.126 mol) in triethylamine (63 g, 0.628 mol) was added a solution of sulfur trioxide pyridine complex (60 g, 0.376 mol) in anhydrous DMSO (300 ml) dropwise over 30 minutes. The resulting mixture was warmed to 50° C. for 30 minutes. The reaction mixture was then cooled to ambient and poured into a mixture of water (1 L) and ethyl acetate (800 ml). The organic layer was separated and the aqueous extracted with ethyl acetate (3×200 ml). The combined organic solutions were then washed with water (3×200 ml), then saturated brine (200 ml), dried (magnesium sulfate), filtered and concentrated. The residue was purified on silica gel, eluting with 5-10% ethyl acetate/petrol. The product was obtained as a white solid (26.2 g, 86%); $^1$H NMR CDCl$_3$ δ 4.07 (4H, s), 4.62 (1H, s), 7.20-7.39 (6H, m), 7.53 (4H, d).

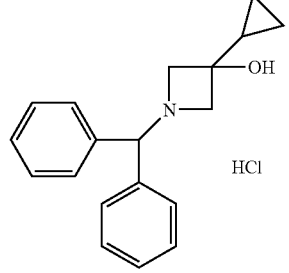

1-Benzhydryl-3-cyclopropylazetidin-3-ol hydrochloride

A solution of cyclopropylmagnesium bromide in THF (0.5M, 600 ml, 0.5 mol) was cooled to −78° C. under a nitrogen atmosphere. Precipitation appeared to occur at this temperature. A solution of N-benzhydrylazetidin-3-one (24.2 g, 0.102 mol) in anhydrous THF (130 ml) was added dropwise over 30 minutes. The mixture was stirred for an additional 90 minutes at −78° C. after which time saturated sodium bicarbonate solution (400 ml) and water (100 ml) were added slowly. The mixture was then diluted with ethyl acetate (1 L) and allowed to warm to ambient. The organic phase was then separated (the aqueous layer was an emulsion of magnesium salts but was easily separable from the organic layer) and the aqueous extracted with ethyl acetate (3×300 ml). The combined organic solutions were then washed with brine saturated (300 ml), dried (magnesium sulfate), filtered and concentrated to give a pale yellow oil. The crude was purified on silica gel, eluting with 20-30% ethyl acetate/petrol. The resulting alcohol (28.3 g) was dissolved in ether (350 ml) and the solution cooled to 0° C. A solution of HCl in ether (2M, 130 ml) was then added dropwise over 15 minutes. The HCl salt precipitated from solution. The resulting slurry was stirred at 0° C. for an additional 10 minutes then filtered. The filter cake was washed with ether (2×100 ml) and the solid dried under vacuum. This furnished the product as a white solid (28.2 g, 88%); $^1$H NMR d$_6$-DMSO δ 0.31-0.50 (4H, m), 1.35 (0.3H, m), 0.51 (0.7H, m), 3.41-4.10 (5H, m), 5.88 (0.3H, d), 6.05 (0.7H, d), 6.35 (1H, brs), 7.30-7.50 (6H, m), 7.61-7.82 (4H, m); ES+ 280.71.

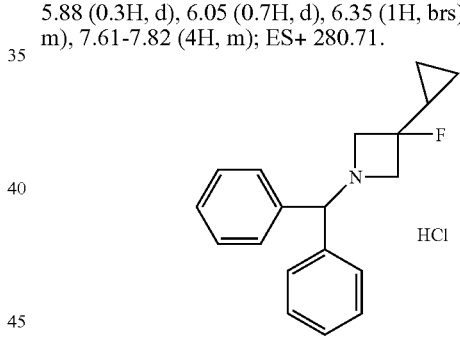

1-Benzhydryl-3-cyclopropyl-3-fluoroazetidine hydrochloride

Saturated NaHCO$_3$ (100 ml) was added to a suspension of 1-Benzhydryl-3-cyclopropylazetidin-3-ol hydrochloride (7.78 g, 24.50 mmol) in ethyl acetate (100 ml). The mixture was transferred to a separating funnel and shaken vigorously until all of the solid had dissolved. The organic layer was separated and the aqueous extracted further with ethyl acetate (50 ml). The combined organic extracts were dried (Na$_2$SO$_4$) and concentrated an oil. The oil was dissolved in dichloromethane (100 ml) and cooled to −78° C. [bis(2-methoxyethyl)amino]sulfur trifluoride (5.98 g, 27.05 mmol, 5.0 ml) was added dropwise and the solution stirred for 30 mins at −78° C. and then warmed to 0° C. and stirred for a further 1 hr. Reaction was quenched with Saturated NaHCO$_3$ (50 ml) and brine (50 ml) and the aqueous layer extracted with dichloromethane (50 ml). The combined organic extracts were dried (Na$_2$SO$_4$) and concentrated to give a yellow oil. The crude was purified on silica gel, eluting with 5% ethyl acetate/petrol. The resulting alcohol was dissolved in ether (100 ml) and the solution cooled to 0° C. A solution of HCl in ether (2M, 25 ml) was then added dropwise over 5 minutes. The HCl salt precipitated from solution. The resulting slurry was stirred at 0° C. for an additional 10 minutes then filtered. The filter cake washed with ether (20 ml) and the solid dried under vacuum. This furnished the product as a white solid (4.71 g, 61%). $^1$H NMR d$_4$-MeOH δ 0.30-0.52 (4H, m), 1.22 (1H, brs), 4.01-4.23 (4H, m), 5.50-5.60 (1H, brs), 7.13-7.46 (10H, m); ES+ 282.

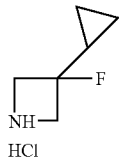

3-cyclopropyl-3-fluoroazetidine hydrochloride

To wet 10% palladium on carbon (Degussa catalyst) under nitrogen was added ethanol (100 ml). A solution of 1-Benzhydryl-3-cyclopropyl-3-fluoroazetidine hydrochloride (6.74 g, 21.23 mmol) in ethanol (50 ml) was added to the catalyst and the mixture hydrogenated at 60 psi on the Parr shaker hydrogenation apparatus for 5 hrs. The reaction was filtered through celite and concentrated to an oil. Ether (50 ml) was added and the mixture cooled to 0° C. and stirred until a precipitate formed. The suspension was filtered and the filter cake washed with ether (20 ml) and the solid dried under vacuum. This furnished the product as an off white solid (3.00 g, 93%). $^1$H NMR d$_6$-DMSO δ 0.52-0.56 (2H, m), 0.59-0.64 (2H, m), 1.35-1.40 (1H, m), 3.91-4.10 (4H, m), 4.01-4.23 (4H, m), 9.50 (1H, brs), 9.63 (1H, brs).

Example 6

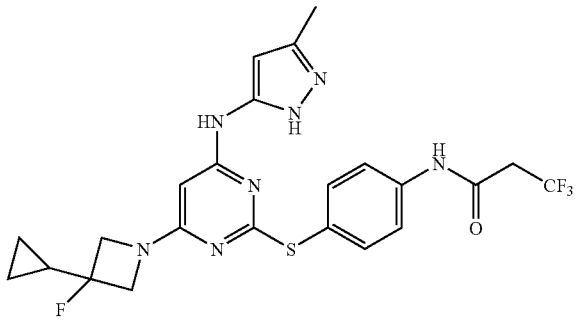

N-(4-(4-(3-methyl-1H-pyrazol-5-ylamino)-6-(3-cyclopropyl-3-fluoroazetidin-1-yl)pyrimidin-2-ylthio) phenyl)-3,3,3-trifluoropropanamide (Compound I-14)

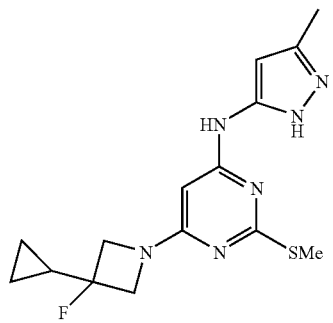

6-(3-cyclopropyl-3-fluoroazetidin-1-yl)-N-(3-methyl-1H-pyrazol-5-yl)-2-(methylthio)pyrimidin-4-amine To a mixture of 6-chloro-N-(3-methyl-1H-pyrazol-5-yl)-2-(methylthio)pyrimidin-4-amine (150 g, 0.58 mol), 3-cyclopropyl-3-fluoroazetidine hydrochloride (132.2 g, 0.87 mol) was added diisopropylethylamine (208 g, 1.61 mol) and isopropanol (1.125 L) and then heated to reflux for 23 hours. The reaction was cooled to slightly hazy solution to 85° C. and filtered and the homogeneous solution concentrated to a minimal volume. EtOAc was added (1 L) and concentrated to minimal volume. EtOAc (1 L) and H$_2$O (1 L) were added and the layers separated (organic started to crystallize product during the extraction). The aqueous layer was further extracted with EtOAc (500 ml). Concentrated the 1st organic to dryness to give a white solid. Hexane (750 ml) was added to the 2nd organic extract and the slurry was stirred at ambient temperature, then cooled to 0° C. for 30 min. Filtered and washed with copious Heptane. The filter cake was dried under vacuum. The filter cake and the white solid from the 1$^{st}$ extraction were combined to afford 155.1 g of the desired product. (155.1 g, 77%). 1H NMR (DMSO, 400 MHz) 0.44 (2H, m), 0.60 (2H, m), 1.38-1.43 (1H, m), 2.18 (3H, s), 2.42 (3H, s), 3.89-3.97 (4H, m), 5.92 (1H, br s), 6.04 (1H, br s), 9.23 (1H, s), 11.86 (1H, s). ES+ 335

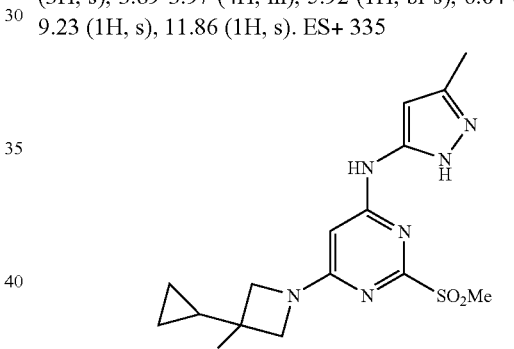

6-(3-cyclopropyl-3-fluoroazetidin-1-yl)-N-(3-methyl-1H-pyrazol-5-yl)-2-(methylsulfonyl)pyrimidin-4-amine A solution of 6-(3-cyclopropyl-3-fluoroazetidin-1-yl)-N-(3-methyl-1H-pyrazol-5-yl)-2-(methylthio)pyrimidin-4-amine (130 g, 389 mmol) in MeOH (5.2 L) was cooled to 0° C. A solution of oxone (526 g, 855 mmol) in H$_2$O (5.2 L) was slowly added to the slurry keeping the temperature below 5° C. After addition the reaction was allowed to warm to room temperature overnight. A 10% solution of NaHSO$_3$ (325 ml) and a 10% solution of K$_2$CO$_3$ (2.6 L) was then added to neutralize the reaction mixture, the solution filtered and the filter cake washed with H$_2$O (3.3 L). The solid was slurried in H$_2$O (2.6 L), the solution filtered and the filter cake washed with H$_2$O (3.3 L). The solid was dried under vacuum (72.3 g, 51%). 1H NMR (DMSO): 0.47 (2H, m), 0.60 (2H, m), 1.43-1.46 (1H, m), 2.20 (3H, s), 3.25 (3H, s), 3.97-4.11 (4H, m), 5.93 (1H, br s), 6.47 (1H, br s). 9.88 (1H, s), 12.01 (1H, br s). ES+ 367

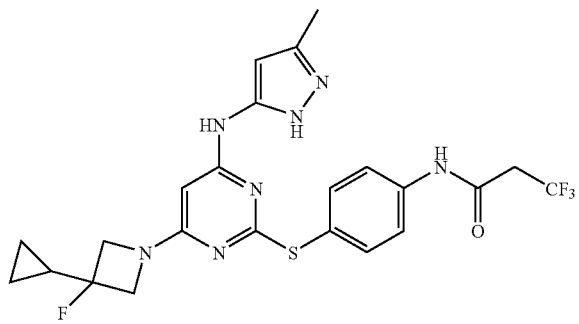

N-(4-(4-(3-methyl-1H-pyrazol-5-ylamino)-6-(3-cyclopropyl-3-fluoroazetidin-1-yl)pyrimidin-2-ylthio)phenyl)-3,3,3-trifluoropropanamide (Compound I-14)

An slurry of 6-(3-cyclopropyl-3-fluoroazetidin-1-yl)-N-(3-methyl-1H-pyrazol-5-yl)-2-(methylsulfonyl)pyrimidin-4-amine (61 g, 170 mmol) and 3,3,3-trifluoro-N-(4-mercaptophenyl)propanamide (41 g, 175 mmol) in CH3CN (1300 mL) was heated to reflux for 1.5 hours. During this time, the slurry transforms from thin and yellowish to thick and brilliant white. The mixture was then cooled to 0° C. and stirred at this temperature for 15 min. Filtered and washed with cold CH$_3$CN (650 mL). The resulting solid was dried for 20 hours at 38° C. under house vacuum. The white solid was charged to a suitable reactor with EtOAc (1300 mL) and NaHCO$_3$ (sat) (1300 mL). The mixture was stirred until no more solid remained. Then, the layers were separated and washed the aqueous with EtOAc (390 mL). The combined organic layers were dried over MgSO4, filtered, washed with EtOAc (130 mL) and concentrated to minimal volume on rotavap. The resulting mixture was re-crystallized out of EtOAc and hexane to give the desired product as a white solid (56.2 g, 72%) 1H NMR (MeOD, 400 MHz): 0.40-0.45 (2H, m), 0.60-0.65 (2H, m), 1.3-1.4 (1H, m), 2.05 (2H, s), 3.25-3.40 (2H, m), 3.85-3.40 (4H, m), 5.40-5.50 (2H, m), 7.50-7.55 (2H, d), 7.65-7.70 (2H, d). ES+ 522.

Table 4 below depicts data for certain exemplary compounds made according to the method described in the General Scheme (Method A) and in Example 6. Compound numbers correspond to those compounds depicted in Table 1.

Example 7

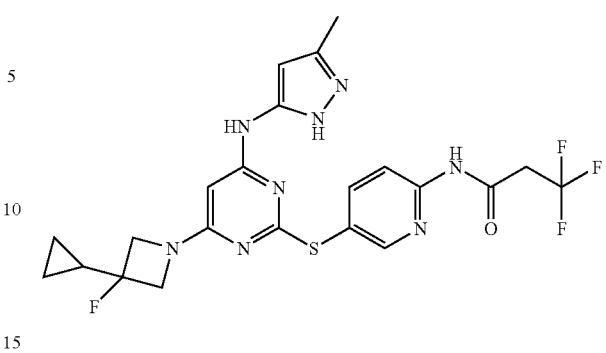

N-(5-(4-(3-methyl-1H-pyrazol-5-ylamino)-6-(3-cyclopropyl-3-fluoroazetidin-1-yl)pyrimidin-2-ylthio)pyridin-2-yl)-3,3,3-trifluoropropanamide (I-21)

To a solution of 2-(6-aminopyridin-3-ylthio)-6-(3-cyclopropyl-3-fluoroazetidin-1-yl)-N-(3-methyl-1H-pyrazol-5-yl)pyrimidin-4-amine (300 mg, 0.7 mmol) and BOC$_2$O (220 mg, 1 mmol) in 4.5 M sodium hydroxide solution (0.470 ml) and DCM (10 ml) was added DMAP (5 mg). The resulting solution was stirred at room temperature for 3 h then washed with sat. NaHCO3 solution, brine, dried (MgSO4), filtered and evaporated in vacuo. Crude product purified by flash chromatography (12 g SiO2, EtOAc/petrol) to give desired intermediate (60 mg, 17%) ES+ 513. This intermediate (60 mg, 0.12 mmol) was dissolved in pyridine (2 ml) and 3,3,3-trifluoropropanoyl chloride (34 mg, 0.23 mmol) was added dropwise and then stirred at room temperature for 30 mins. A further 3 drops of 3,3,3-trifluoropropanoyl chloride were added to give complete conversion to product after stirring for further 30 mins. The reaction mixture was then concentrated in vacuo, residue redissolved in DCM (2 ml)/TFA (1 ml) and stirred at room temperature for 2 h. The mixture was concentrated in vacuo and crude product purified by preparative LCMS and freeze-dried (MeCN/H$_2$O/TFA) to give title compound as a white solid and TFA salt (25 mg, 33%). 1H NMR (DMSO-d6) 0.20-0.21 (2H, m), 0.36-0.38 (2H, m), 1.15-1.20 (1H, m), 1.77 (3H, s), 3.40-3.50 (2H, m), 3.57-3.72 (4H, m), 5.10-5.15 (12H, s), 7.75-7.80 (1H, d), 7.92-7.97 (1H, d), 8.22 (1H, s), 9.20 (1H, s), 10.91 (1H, s). ES+ 523.

The experimentals shown below describe the preparation of some of the compounds used in the examples described herein.

TABLE 4

| Compound No | M + 1 (obs) | 1H NMR | Rt(mins) |
| --- | --- | --- | --- |
| I-14 | 522.00 | (MeOD): 0.40-0.45(2H, m), 0.60-0.65(2H, m), 1.3-1.4(1H, m), 2.05(2H, s), 3.25-3.40(2H, m), 3.85-3.40(4H, m), 5.40-5.50(2H, m), 7.50-7.55(2H, d), 7.65-7.70(2H, d). | 9.235 |
| I-18 | 498.70 | (DMSO-d6): 0.45-0.48(2H, m), 0.6-0.63(2H, m), 0.87-0.92(4H, m), 1.45(1H, brs), 1.82-1.85(1H, m), 2.02(3H, s), 3.8-3.95(4H, m), 5.3(1H, vbrs), 5.75(1H, brs), 7.4(1H, d), 7.52-7.55(1H, m), 7.8(1H, d), 9.4(1H, brs), 10.7(1H, brs), 11.7(1H, brs) | 9.2 |
| I-20 | 516.60 | (DMSO-d6): 0.22-0.25(2H, m), 0.42-0.45(2H, m), 1.20-1.26(1H, m), 1.75-1.9(5H, m), 2.6-2.7(1H, m), 3.65-3.8(4H, m), 5.1(1H, brs), 5.4(1H, vbrs), 7.3(2H, d), 7.52(2H, d), 9.1(1H, brs), 10.4(1H, s), 11.5(1H, brs) | 9.34 |

Compound a

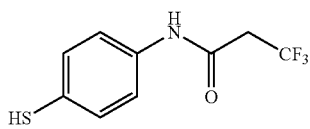

3,3,3-trifluoro-N-(4-mercaptophenyl)propanamide

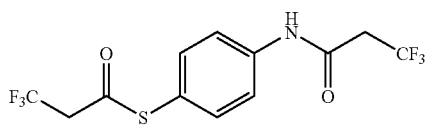

S-4-(3,3,3-trifluoropropanamido)phenyl 3,3,3-trifluoropropanethioate

4-Aminothiophenol was melted and charged to a flask. Degassed EtOAc (1950 mL) was added. A solution of $K_2CO_3$ (92 g, 670 mmol) in degassed $H_2O$ (1300 vol) was added. The solution was cooled to 0° C. and the 3,3,3-trifluoropropanoyl chloride (55.2 g, 600 mmol) was slowly added to keep the temperature below 10° C.). The reaction was warmed to rt. The organic layer was separated and washed with brine (1300 mL). Then concentrated on the rotary evaporator. The solid was slurried in Heptane/EtOAc (390 mL/390 mL) for 30 min. Heptane (780 mL) was added and the slurry was cooled to 0° C. for 30 min. The slurry was filtered. The filter cake is dried under vacuum to give the desired compound (51.3 g, 87.2%).

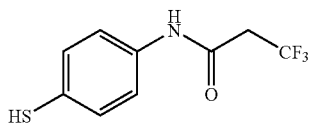

3,3,3-trifluoro-N-(4-mercaptophenyl)propanamide

S-4-(3,3,3-trifluoropropanamido)phenyl 3,3,3-trifluoropropanethioate (44.8 g, 189 mmol) and EtOH (70 mL) were charged to a flask. Concentrated HCl (22.5 mL) was slowly added to keep the temperature below 30° C. The reaction was then heated to 50° C. for 17.5 h. The reaction mixture was reduced to 41 mL by vacuum distillation at 50° C. Cool the reaction to room temperature and $H_2O$ (51 mL) was added. The slurry was filtered and the filter cake washed with H2O (3×35 mL). The solid was dried under vacuum to produce the desired compound (19.9 g, 58%).

Example 9

Aurora-2 (Aurora A) Inhibition Assay

Compounds were screened for their ability to inhibit Aurora-2 using a standard coupled enzyme assay (Fox et al., Protein Sci., (1998) 7, 2249). Assays were carried out in a mixture of 100 mM Hepes (pH7.5), 10 mM $MgCl_2$, 1 mM DTT, 25 mM NaCl, 2.5 mM phosphoenolpyruvate, 300 µM NADH, 30 µg/ml pyruvate kinase and 10 µg/ml lactate dehydrogenase. Final substrate concentrations in the assay are 400 µM ATP (Sigma Chemicals) and 570 µM peptide (Kemptide, American Peptide, Sunnyvale, Calif.). Assays were carried out at 30° C. and in the presence of 40 nM Aurora-2.

An assay stock buffer solution was prepared containing all of the reagents listed above, with the exception of Aurora-2 and the test compound of interest. 55 µl of the stock solution was placed in a 96 well plate followed by addition of 2 µl of DMSO stock containing serial dilutions of the test compound (typically starting from a final concentration of 7.5 µM). The plate was preincubated for 10 minutes at 30° C. and the reaction initiated by addition of 10 µl of Aurora-2. Initial reaction rates were determined with a Molecular Devices SpectraMax Plus plate reader over a 10 minute time course. IC50 and Ki data were calculated from non-linear regression analysis using the Prism software package (GraphPad Prism version 3.0cx for Macintosh, GraphPad Software, San Diego Calif., USA).

Example 10

Aurora-1 (Aurora B) Inhibition Assay(Radiometric)

An assay buffer solution was prepared which consisted of 25 mM HEPES (pH 7.5), 10 mM $MgCl_2$, 0.1% BSA and 10% glycerol. A 22 nM Aurora-B solution, also containing 1.7 mM DTT and 1.5 mM Kemptide (LRRASLG), was prepared in assay buffer. To 22 µL of the Aurora-B solution, in a 96-well plate, was added 2 µl of a compound stock solution in DMSO and the mixture allowed to equilibrate for 10 minutes at 25° C. The enzyme reaction was initiated by the addition of 16 µl stock [γ-$^{33}$P]-ATP solution (~20 nCi/µL) prepared in assay buffer, to a final assay concentration of 800 µM. The reaction was stopped after 3 hours by the addition of 16 µL 500 mM phosphoric acid and the levels of $^{33}$P incorporation into the peptide substrate were determined by the following method.

A phosphocellulose 96-well plate (Millipore, Cat no. MAPHNOB50) was pre-treated with 100 µL of a 100 mM phosphoric acid prior to the addition of the enzyme reaction mixture (40 µL). The solution was left to soak on to the phosphocellulose membrane for 30 minutes and the plate subsequently washed four times with 200 µL of a 100 mM phosphoric acid. To each well of the dry plate was added 30 µL of Optiphase 'SuperMix' liquid scintillation cocktail (Perkin Elmer) prior to scintillation counting (1450 Microbeta Liquid Scintillation Counter, Wallac). Levels of non-enzyme catalyzed background radioactivity were determined by adding 16 µL of the 500 mM phosphoric acid to control wells, containing all assay components (which acts to denature the enzyme), prior to the addition of the [γ-$^{33}$P]-ATP solution. Levels of enzyme catalyzed $^{33}$P incorporation were calculated by subtracting mean background counts from those measured at each inhibitor concentration. For each Ki determination 8 data points, typically covering the concentration range 0-10 µM compound, were obtained in duplicate (DMSO stocks were prepared from an initial compound stock of 10 mM with subsequent 1:2.5 serial dilutions). Ki values were calculated from initial rate data by non-linear regression using the Prism software package (Prism 3.0, Graphpad Software, San Diego, Calif.).

Example 11

Itk Inhibition Assay: Radioactivity-Based Assay

The compounds of the present invention were evaluated as inhibitors of human Itk kinase using a radioactivity-based assay.

Assays were carried out in a mixture of 20 mM MOPS (pH 7.0), 10 mM $MgCl_2$, 0.1% BSA and 1 mM DTT. Final substrate concentrations in the assay were 7.5 µM [γ-$^{33}$P]ATP (400 Ci $^{33}$P ATP/µmol ATP, Amersham Pharmacia Biotech/Sigma Chemicals) and 3 µM peptide (SAM68 protein Δ332-443). Assays were carried out at 25° C. in the presence of 50 nM Itk. An assay stock buffer solution was prepared containing all of the reagents listed above, with the exception of ATP and the test compound of interest. 50 µL of the stock solution was placed in a 96 well plate followed by addition of 2 µL of DMSO stock containing serial dilutions of the test compound (typically starting from a final concentration of 50 µM with 2-fold serial dilutions) in duplicate (final DMSO concentration 2%). The plate was pre-incubated for 10 minutes at 25° C. and the reaction initiated by addition of 50 µL [γ-$^{33}$P]ATP (final concentration 7.5 µM).

The reaction was stopped after 10 minutes by the addition of 100 µL 0.2M phosphoric acid+0.01% TWEEN 20. A multiscreen phosphocellulose filter 96-well plate (Millipore, Cat no. MAPHNOB50) was pretreated with 100 µL 0.2M phosphoric acid+0.01% TWEEN 20 prior to the addition of 170 µL of the stopped assay mixture. The plate washed with 4×200 µL 0.2M phosphoric acid+0.01% TWEEN 20. After drying, 30 µL Optiphase 'SuperMix' liquid scintillation cocktail (Perkin Elmer) was added to the well prior to scintillation counting (1450 Microbeta Liquid Scintillation Counter, Wallac).

Ki(app) data were calculated from non-linear regression analysis of the initial rate data using the Prism software package (GraphPad Prism version 3.0cx for Macintosh, GraphPad Software, San Diego Calif., USA).

Example 12

JAK3 Inhibition Assay

Compounds were screened for their ability to inhibit JAK using the assay shown below. Reactions were carried out in a kinase buffer containing 100 mM HEPES (pH 7.4), 1 mM DTT, 10 mM MgCl$_2$, 25 mM NaCl, and 0.01% BSA. Substrate concentrations in the assay were 5 µM ATP (200 uCi/µmole ATP) and 1 µM poly(Glu)$_4$Tyr. Reactions were carried out at 25° C. and 1 nM JAK3.

To each well of a 96 well polycarbonate plate was added 1.5 µl of a candidate JAK3 inhibitor along with 50 µl of kinase buffer containing 2 µM poly(Glu)$_4$Tyr and 10 µM ATP. This was then mixed and 50 µl of kinase buffer containing 2 nM JAK3 enzyme was added to start the reaction. After 20 minutes at room temperature (25C), the reaction was stopped with 50 µl of 20% trichloroacetic acid (TCA) that also contains 0.4 mM ATP. The entire contents of each well were then transferred to a 96 well glass fiber filter plate using a TomTek Cell Harvester. After washing, 60 µl of scintillation fluid was added and $^{33}$P incorporation detected on a Perkin Elmer TopCount.

Example 13

JAK2 Inhibition Assay

The assays are as described above in Example 13 except that JAK-2 enzyme was used, the final poly(Glu)$_4$Tyr concentration was 15 µM, and final ATP concentration was 12 µM.

Example 14

FLT-3 Inhibition Assay

Compounds were screened for their ability to inhibit FLT-3 activity using a radiometric filter-binding assay. This assay monitors the 33P incorporation into a substrate poly(Glu, Tyr) 4:1 (pE4Y). Reactions were carried out in a solution containing 100 mM HEPES (pH 7.5), 10 mM MgCl$_2$, 25 mM NaCl, 1 mM DTT, 0.01% BSA and 2.5% DMSO. Final substrate concentrations in the assay were 90 µM ATP and 0.5 mg/ml pE4Y (both from Sigma Chemicals, St Louis, Mo.). The final concentration of a compound of the present invention was generally between 0.01 and 5 µM. Typically, a 12-point titration was conducted by preparing serial dilutions from 10 mM DMSO stock of test compound. Reactions were carried out at room temperature.

Two assay solutions were prepared. Solution 1 contains 100 mM HEPES (pH 7.5), 10 mM MgCl$_2$, 25 mM NaCl, 1 mg/ml pE4Y and 180 mM ATP(containing 0.3 mCi of [γ-33$^P$] ATP for each reaction). Solution 2 contains 100 mM HEPES (pH 7.5), 10 mM MgCl$_2$, 25 mM NaCl, 2 mM DTT, 0.02% BSA and 3 nM FLT-3. The assay was run on a 96 well plate by mixing 50 µl each of Solution 1 and 2.5 ml of the compounds of the present invention. The reaction was initiated with Solution 2. After incubation for 20 minutes at room temperature, the reaction was stopped with 50 µl of 20% TCA containing 0.4 mM of ATP. All of the reaction volume was then transferred to a filter plate and washed with 5% TCA by a Harvester 9600 from TOMTEC (Hamden, Conn.). The amount of $^{33}$P incorporation into pE4y was analyzed by a Packard Top Count Microplate Scintillation Counter (Meriden, Conn.). The data was fitted using Prism software to get an IC$_{50}$ or Ki.

Example 15

Microsomal Stability Assay

Microsomal stability was monitored by generation of depletion-time profiles in microsomes from a range of species (male CD-1 mouse, male Sprague-Dawley rat, male Beagle dog, male Cynomolgus monkey and pooled mixed gender human). Compound spiking solutions were made up by diluting down the compound stock solution in DMSO (typically 10 mM) to give a solution in acetonitrile (0.5 mM). Compound (to give final concentration of 5 µM) was incubated with a final reaction mixture (1000 µL) consisting of liver microsome protein (1 mg/mL) and a β-nicotinamide adenine dinucleotide phosphate, reduced form (NADPH)-regenerating system (RGS) [consisting of 2 mM β-nicotinamide adenine dinucleotide phosphate (NADP), 20.5 mM isocitric acid, 0.5 U of isocitric dehydrogenase/mL, 30 mM magnesium chloride, and 0.1 M phosphate buffer (PB) pH 7.4] in the presence of 0.1 M PB (pH 7.4).

The reaction was initiated by the addition (250 µL) of the pre-incubated RGS to the pre-incubated microsome/VRT/PB mixture (pre-incubation in both instances was for 10 minutes at 37° C.). Samples were incubated within Eppendorf vials (1.5 ml) on a heater shaker (DPC Micromix 5 (settings; form 20, amplitude 4) modified to be heated, to 37° C., by two plate heaters fixed to the deck and controlled by a Packard Manual Heater) attached to a Multiprobe II HT Ex automated liquid handler. The liquid handler was programmed (WinPREP software) to sample the microsomal incubation mixture after 0, 2, 10, 30 and 60 minutes of incubation and transfer an aliquot (100 µL) to a stop block (96-well block) containing 100 µL of chilled methanol. The % organic in the stop mixture was optimized for analysis by addition of appropriate volumes of aqueous/organic (typically 100 µL of 50:50 methanol:water).

Prior to analysis the stop block was placed on a shaker (DPC Micromix 5; 10 min, form 20, amplitude 5) to precipitate out proteins. The block was then centrifuged (Jouan GR412; 2000 rpm, 15 min, 4° C.). A sample aliquot (200 µL) was then transferred to an analysis block and the block was centrifuged again (Jouan GR412; 2000 rpm, 5 min, 4° C.) prior to being sent for analysis. Depletion profiles were determined by monitoring the disappearance of VRT by liquid chromatography-tandem mass spectrometry (LC-MS/MS). Samples were injected (20 μL; Agilent 1100 liquid chromatographic system equipped with autosampler) onto an analytical column. Mobile phase consisted of Water+0.05% (v/v) formic acid (A) and methanol+0.05% (v/v) formic acid (B).

Running a gradient method optimized for the compound of interest carried out the compound elution from analytical column. The total run time was 6 minutes with a flow rate of 0.35 mL/min. The entire column effluent entered the electrospray ionization source (positive mode) of a Micromass Quattro LC tandem mass spectrometer between 0.5 and 5.9 min of the run. The mass spectrometry was optimized for the compound of interest. All incubations were conducted in duplicate and results were expressed as % parent remaining at either 30 minutes or 60 minutes relative to 0 minutes sample.

Example 16

Analysis of Cell Proliferation and Viability

Compounds were screened for their ability to inhibit cell proliferation and their effects on cell viability using Colo205 cells obtained from ECACC and using the assay shown below.

Colo205 cells were seeded in 96 well plates and serially diluted compound was added to the wells in duplicate. Control groups included untreated cells, the compound diluent (0.1% DMSO alone) and culture medium without cells. The cells were then incubated for 72 or 96 hrs at 37 C in an atmosphere of 51 CO2/95% humidity.

To measure proliferation, 3 h prior to the end of the experiment 0.5 μCi of 3H thymidine was added to each well. Cells were then harvested and the incorporated radioactivity counted on a Wallac microplate beta-counter. Cell viability was assessed using Promega CellTiter 96AQ to measure MTS conversion. Dose response curves were calculated using either Prism 3.0 (GraphPad) or SoftMax Pro 4.3.1 LS (Molecular Devices) software.

Example 17

Abl Kinase Activity Inhibition Assay and Determination of the Inhibition Constant Ki Compounds were screened for their ability to inhibit N-terminally truncated (Δ 27) Abl kinase activity using a standard coupled enzyme system (Fox et al., *Protein Sci.*, 7, pp. 2249 (1998)). Reactions were carried out in a solution containing 100 mM HEPES (pH 7.5), 10 mM $MgCl_2$, 25 mM NaCl, 300 μM NADH, 1 mM DTT and 3% DMSO. Final substrate concentrations in the assay were 110 μM ATP (Sigma Chemicals, St Louis, Mo.) and 70 μM peptide (EAIYAAPFAKKK, American Peptide, Sunnyvale, Calif.). Reactions were carried out at 30° C. and 21 nM Abl kinase. Final concentrations of the components of the coupled enzyme system were 2.5 mM phosphoenolpyruvate, 200 μM NADH, 60 μg/ml pyruvate kinase and 20 μg/ml lactate dehydrogenase.

An assay stock buffer solution was prepared containing all of the reagents listed above with the exception of ATP and the test compound of interest. The assay stock buffer solution (60 μl) was incubated in a 96 well plate with 2 μl of the test compound of interest at final concentrations typically spanning 0.002 μM to 30 μM at 30° C. for 10 min. Typically, a 12 point titration was prepared by serial dilutions (from 1 mM compound stocks) with DMSO of the test compounds in daughter plates. The reaction was initiated by the addition of 5 μl of ATP (final concentration 110 μM). Rates of reaction were obtained using a Molecular Devices Spectramax plate reader (Sunnyvale, Calif.) over 10 min at 30° C. The Ki values were determined from the residual rate data as a function of inhibitor concentration using nonlinear regression (Prism 3.0, Graphpad Software, San Diego, Calif.).

Example 18

Mutant Abl Kinase (T315I) Activity Inhibition Assay and Determination of the Inhibition Constant IC50

Compounds were screened for their ability to inhibit the T315I mutant form of human Abl at Upstate Cell Signaling Solutions (Dundee, UK). In a final reaction volume of 25 μl, the T315I mutant of human Abl (5-10 mU) was incubated with 8 mM MOPS pH 7.0, 0.2 mM EDTA, 50 μM EAIYAAP-FAKKK, 10 mM Mg Acetate, [γ-$^{33}$P-ATP] (specific activity approx. 500 cpm/pmol, 10 mM final assay concentration) and the test compound of interest at final concentrations over the range 0-4 μnM. The reaction was initiated by the addition of the MgATP mix. After incubation for 40 minutes at room temperature, the reaction was stopped by the addition of 5 μl of a 3% phosphoric acid solution. 10 μl of the reaction was then spotted onto a P30 filtermat and washed three times for 5 minutes in 75 mM phosphoric acid and once in methanol prior to drying and scintillation counting. Inhibition IC50 values were determined from non-linear regression analysis of the residual enzyme activities as a function of inhibitor concentration (Prism 3.0, Graphpad Software, San Diego, Calif.).

Example 19

Plk4 Inhibition Assay

Compounds were screened for their ability to inhibit Plk4 using a radioactive-phosphate incorporation assay. Assays were carried out in a mixture of 8 mM MOPS (pH 7.5), 10 mM $MgCl_2$, 0.1% BSA and 2 mM DTT. Final substrate concentrations were 15 μM [γ-33P]ATP (227 mCi 33P ATP/mmol ATP, Amersham Pharmacia Biotech/Sigma Chemicals) and 300 μM peptide (KKKMDATFADQ). Assays were carried out at 25° C. in the presence of 25 nM Plk4. An assay stock buffer solution was prepared containing all of the reagents listed above, with the exception of ATP and the test compound of interest. 30 μL of the stock solution was placed in a 96 well plate followed by addition of 2 μL of DMSO stock containing serial dilutions of the test compound (typically starting from a final concentration of 10 μM with 2-fold serial dilutions) in duplicate (final DMSO concentration 5%). The plate was pre-incubated for 10 minutes at 25° C. and the reaction initiated by addition of 8 μL [γ-33P]ATP (final concentration 15 μM). The reaction was stopped after 180 minutes by the addition of 100 μL 0.14M phosphoric acid. A multiscreen phosphocellulose filter 96-well plate (Millipore, Cat no. MAPHN0B50) was pretreated with 100 μL 0.2M phosphoric acid prior to the addition of 125 μL of the stopped assay mixture. The plate was washed with 4×200 μL 0.2M phosphoric acid. After drying, 100 μL Optiphase 'SuperMix' liquid scintillation cocktail (Perkin Elmer) was added to the well prior to scintillation counting (1450 Microbeta Liquid Scintillation Counter, Wallac). After removing mean background values for all of the data points, Ki(app) data were calculated from non-linear regression analysis of the initial rate data using the Prism software package (GraphPad Prism version 3.0cx for Macintosh, GraphPad Software, San Diego Calif., USA).

Example 20

FGFR1, MLK1, Tie2, and TrkA Inhibition Assay

Compound(s) were screened for their ability to inhibit Arg (Abl-2), FGFR1, MLK1, Tie2, and TrkA using screening methods known to one of ordinary skill in the art. All of the above enzymes were screened with ATP concentrations at or close to the $K_m$ for ATP.

Table 5 below depicts the IC50 values obtained from Example 20:

TABLE 5

| Compound No | Arg IC50 (uM) | FGFR1 IC50 (uM) | MLK1 IC50 (uM) | Tie2 IC50 (uM) | TrkA IC50 (uM) |
|---|---|---|---|---|---|
| I-14 | 0.014 | 0.121 | 0.027 | 0.089 | 0.018 |
| I-17 | 0.21 | 0.088 | — | — | — |
| I-18 | 0.053 | 0.022 | — | — | — |
| I-19 | 0.13 | 0.035 | — | — | — |

Table 6 below depicts Ki values obtained from Example 20:

TABLE 6

| Compound No | Arg IC50 (uM) | FGFR1 IC50 (uM) | MLK1 IC50 (uM) | Tie2 IC50 (uM) | TrkA IC50 (uM) |
|---|---|---|---|---|---|
| I-14 | 0.0033 | 0.065 | 0.014 | 0.047 | 0.005 |

Table 7 below depicts data from Examples 9, 10, and 16 described above.

TABLE 7

| Compound No | Aurora A Ki (uM) | Aurora B Ki (uM) | Colo205 inh 3H-Thy incorporation after 72 hours IC50 (uM) | Colo205 inh 3H-Thy incorporation after 96 hours IC50 (uM) |
|---|---|---|---|---|
| I-1 | 0.00040 | 0.007 | — | 0.047 |
| I-2 | 0.00039 | 0.0076 | 0.026 | 0.026 |
| I-3 | 0.00067 | 0.0065 | 0.002 | 0.004 |
| I-4 | 0.0017 | 0.015 | — | 0.092 |
| I-5 | 0.0012 | 0.014 | — | 0.033 |
| I-6 | 0.00077 | 0.0062 | — | 0.024 |
| I-7 | 0.00036 | <0.006 | — | 0.022 |
| I-8 | 0.00087 | 0.0071 | 0.04 | 0.033 |
| I-9 | 0.00043 | <0.006 | — | 0.016 |
| I-10 | 0.00042 | 0.007 | — | 0.042 |
| I-11 | 0.00041 | 0.009 | — | 0.028 |
| I-12 | 0.00035 | 0.003 | 0.019 | — |
| I-13 | 0.0011 | 0.022 | 0.072 | 0.039 |
| I-14 | 0.00035 | 0.0068 | 0.006 | 0.006 |
| I-15 | 0.00040 | 0.0096 | 0.026 | — |
| I-16 | 0.0010 | 0.024 | 0.051 | — |
| I-17 | 0.00062 | 0.012 | 0.026 | 0.019 |
| I-18 | 0.00035 | 0.018 | 0.027 | — |
| I-19 | 0.00044 | 0.021 | 0.05 | — |
| I-20 | 0.00077 | 0.018 | 0.012 | — |
| I-21 | 0.00044 | 0.0095 | 0.02 | — |

Table 8 below depicts data from Examples 12-14 and 17-18.

TABLE 8

| Compound Number | FLT-3 Ki (uM) | JAK-2 Ki (uM) | JAK-3 Ki (uM) | Abl (T315I) Ki (uM) | Abl (wild) Ki (uM) |
|---|---|---|---|---|---|
| I-1 | — | — | — | 0.43 | — |
| I-2 | 0.036 | 0.026 | 0.16 | — | 0.064 |
| I-3 | 0.026 | 0.034 | 0.15 | — | 0.030 |
| I-4 | — | — | — | — | — |
| I-5 | 0.021 | 0.026 | 0.1 | — | — |
| I-6 | 0.048 | 0.044 | 0.19 | — | — |
| I-7 | 0.023 | 0.023 | 0.037 | — | — |
| I-8 | 0.028 | 0.041 | 0.14 | — | 0.030 |
| I-9 | 0.11 | 0.022 | 0.15 | — | — |
| I-10 | 0.0025 | 0.054 | 0.051 | — | — |
| I-11 | 0.02 | 0.015 | 0.056 | — | — |
| I-12 | 0.015 | 0.0029 | 0.028 | — | — |
| I-13 | 0.043 | 0.11 | 0.29 | 0.21 | 0.088 |
| I-14 | 0.065 | 0.011 | 0.077 | 0.033 | 0.023 |
| I-15 | — | — | — | 0.2 | 0.057 |
| I-16 | — | — | — | 0.18 | 0.17 |
| I-17 | — | — | — | 0.053 | 0.022 |
| I-18 | 0.16 | 0.36 | 0.22 | — | — |
| I-19 | 0.14 | 0.13 | 0.62 | — | — |
| I-20 | 0.072 | 0.051 | 0.11 | — | — |
| I-21 | 0.12 | 0.028 | 0.1 | — | — |

While we have described a number of embodiments of this invention, it is apparent that our basic examples may be altered to provide other embodiments that utilize or encompass the compounds, methods, and processes of this invention. Therefore, it will be appreciated that the scope of this invention is to be defined by the appended claims.

We claim:
1. A compound of formula ii-d:

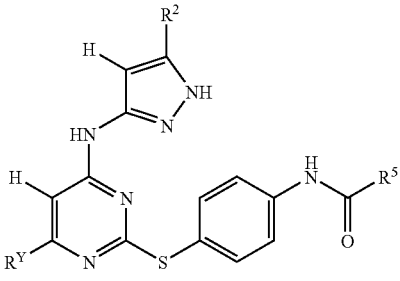

ii-d or a pharmaceutically acceptable salt thereof, wherein:
$R^2$ is $C_{1-3}$ alkyl or cyclopropyl;
$R^5$ is $CH_2CH_3$, $CH_2CF_3$, $CH_2CH_2CF_3$,

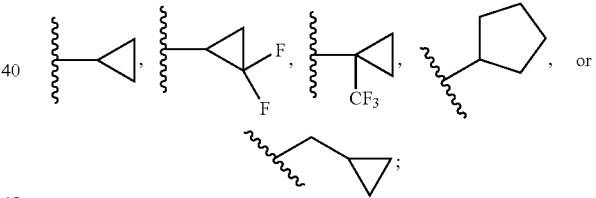

$R^y$ is

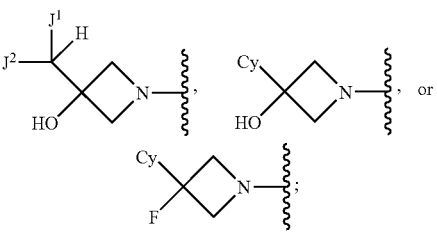

$J^1$ is H or $CH_3$;
$J^2$ is $C_{1-4}$ alkyl; and
Cy is $C_{3-5}$ cycloalkyl.

2. The compound of claim 1, wherein $R^5$ is selected from $CH_2CF_3$, $CH_2CH_2CF_3$,

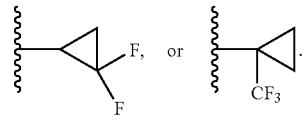

3. The compound of claim 2, wherein $R^5$ is selected from $CH_2CF_3$ or

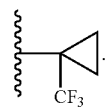

4. The compound of claim 3, wherein $R^5$ is $CH_2CF_3$.
5. The compound according to claim 1, wherein $R^Y$ is

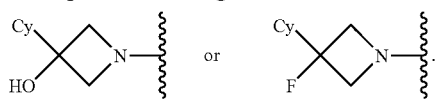

6. The compound according to claim 5, wherein $R^Y$ is

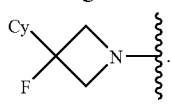

7. The compound according to claim 6, wherein Cy is cyclopropyl.
8. The compound according to claim 1, wherein $R^2$ is methyl.
9. A compound selected from the following compounds:

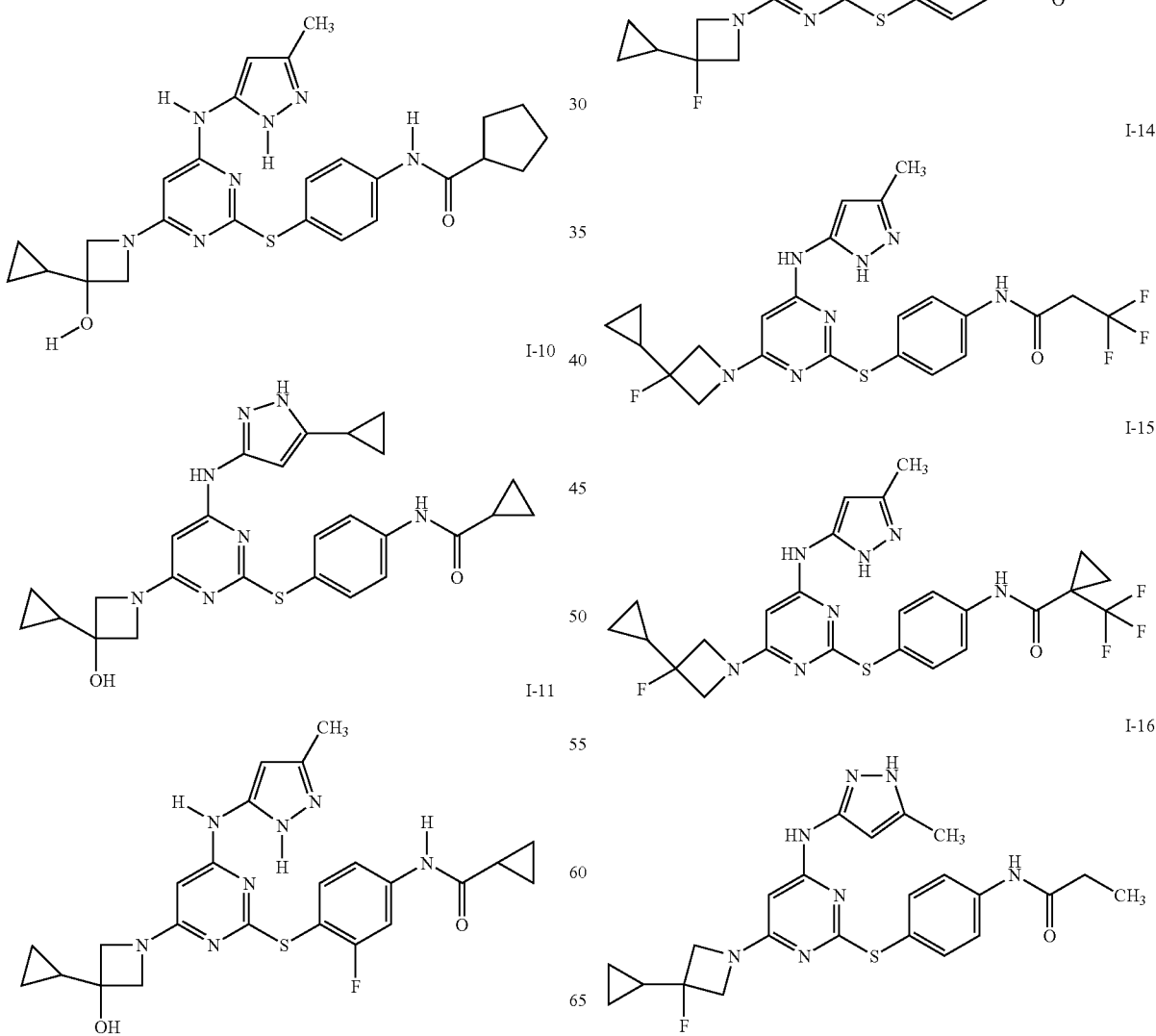

-continued
I-17
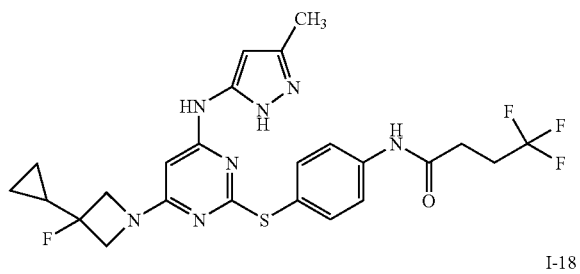
I-18
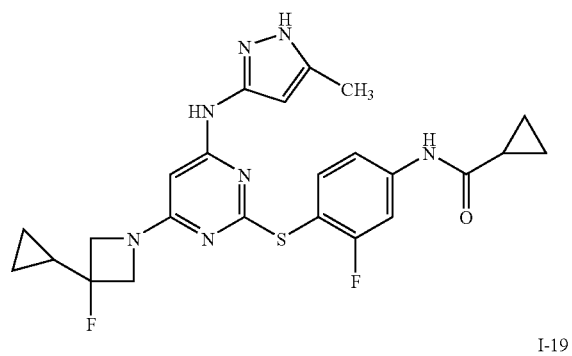
I-19
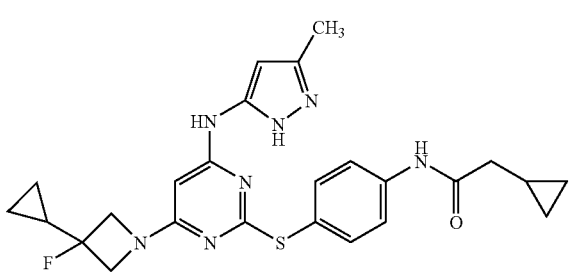
-continued
I-20
I-21
10. A composition comprising a compound of any one of claims 1-8 or 9 and a pharmaceutically acceptable carrier, adjuvant, or vehicle.
11. A method of treating a proliferative disorder in a patient comprising the step of administering to said patient a compound of any one of claims 1-8 or 9, wherein the proliferative disorder is colon cancer.
\* \* \* \* \*